US012733801B2

(12) United States Patent
Guo et al.

(10) Patent No.: US 12,733,801 B2
(45) Date of Patent: Sep. 15, 2026

(54) PORTABLE AUTOMATIC CONTROL SYSTEM FOR CAPSULE ENDOSCOPY IN STOMACH

(71) Applicant: Hong Kong Applied Science and Technology Research Institute Company Limited, Hong Kong (HK)

(72) Inventors: Huimin Guo, Hong Kong (HK); Wenchao Wu, Hong Kong (HK); Chun Kit Lau, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 240 days.

(21) Appl. No.: 18/581,563

(22) Filed: Feb. 20, 2024

(65) Prior Publication Data

US 2025/0261833 A1 Aug. 21, 2025

(51) Int. Cl.

*A61B 1/00* (2006.01)
*A61B 1/04* (2006.01)

(Continued)

(52) U.S. Cl.

CPC .......... *A61B 1/041* (2013.01); *A61B 1/00158* (2013.01); *A61B 5/062* (2013.01); *A61B 34/20* (2016.02)

(58) Field of Classification Search

CPC ..... A61B 1/041; A61B 1/00158; A61B 5/062; A61B 34/20; A61B 1/00016;

(Continued)

(56) References Cited

U.S. PATENT DOCUMENTS 8,771,175 B2 7/2014 Schostek et al.
9,445,711 B2 9/2016 Sitti et al.

(Continued)

FOREIGN PATENT DOCUMENTS

CN 104146676 A 11/2014
CN 206576844 U 10/2017

(Continued)

OTHER PUBLICATIONS

Shamsudhin, Navneen et al., "Magnetically guided capsule endoscopy", Jun. 23, 2017, Medical Phys. 44 (8).*
ISR and Written Opinion, PCT/CN2024/080044, Nov. 13, 2024.

*Primary Examiner* — Baisakhi Roy
(74) *Attorney, Agent, or Firm* — gPatent LLC; Stuart T. Auvinen

(57) ABSTRACT

An automated magnetic endoscopy machine has a stationary disk that a person stands on that is surrounded by a rotating ring that has two telescoping poles, each having an electromagnet assembly with an actuator to raise and lower the electromagnet. Magnet current drivers adjust currents to the electromagnet to allow increased attraction to horizontally pull a swallowed capsule in the person's stomach. One actuator can move to a higher Z position than the other to pitch the capsule up, allowing imaging out of the horizontal plane. The rotating ring allows the electromagnets to rotate around a vertical axis. A sequence of rotational, Z, and radial/horizontal movements are performed by a control program that moves the capsule along paths in the stomach to capture images from cameras inside the capsule. The control program uses a laser in the capsule to map stomach walls before plotting paths through the stomach for imaging.

20 Claims, 20 Drawing Sheets

(51) Int. Cl.

| | |
|---|---|
| ***A61B 1/045*** | (2006.01) |
| ***A61B 1/06*** | (2006.01) |
| ***A61B 5/06*** | (2006.01) |
| ***A61B 34/20*** | (2016.01) |

(58) Field of Classification Search
CPC . A61B 1/00177; A61B 1/00181; A61B 1/045; A61B 1/068
See application file for complete search history.

(56) References Cited

U.S. PATENT DOCUMENTS

2007/0221233 A1* 9/2007 Kawano ................. A61B 5/073 128/899
2008/0300453 A1* 12/2008 Aoki .................. A61B 1/00158 600/118
2010/0268025 A1* 10/2010 Belson ............... A61B 1/00158 600/109
2011/0060189 A1* 3/2011 Belson ................... A61B 34/73 600/117
2011/0301497 A1* 12/2011 Shachar ................. A61B 1/041 600/114
2014/0155709 A1* 6/2014 Ikai .................... A61B 1/00158 600/302
2017/0164816 A1* 6/2017 Kawano ................. G02B 23/24
2018/0084976 A1* 3/2018 Duan ..................... A61B 5/062
2019/0320884 A1 10/2019 Duan et al.
2020/0100658 A1* 4/2020 Abbott ................. A61B 1/0051
2020/0337533 A1 10/2020 Wang et al.
2023/0039420 A1 2/2023 Wang et al.

FOREIGN PATENT DOCUMENTS

CN 107886503 A 4/2018
CN 111568349 A 8/2020
CN 112842230 A 5/2021
CN 114587241 A 6/2022

* cited by examiner

REAR VIEW

REAR VIEW 30
32
S
N
S
N
20
22
10
S
N
MOVE UP(+Z)
Z
X
REAR VIEW
30
32
10
S
N
S
N
S
N
20
22
MOVE DOWN (-Z)

FIG. 11A
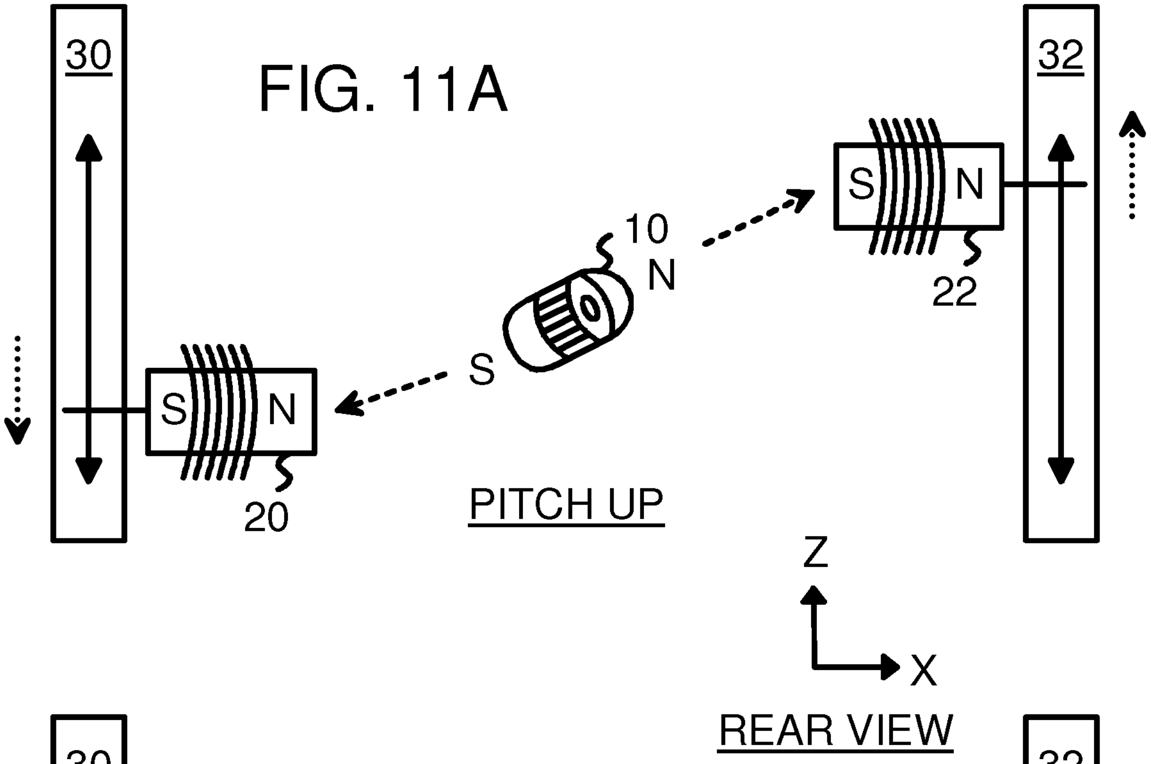
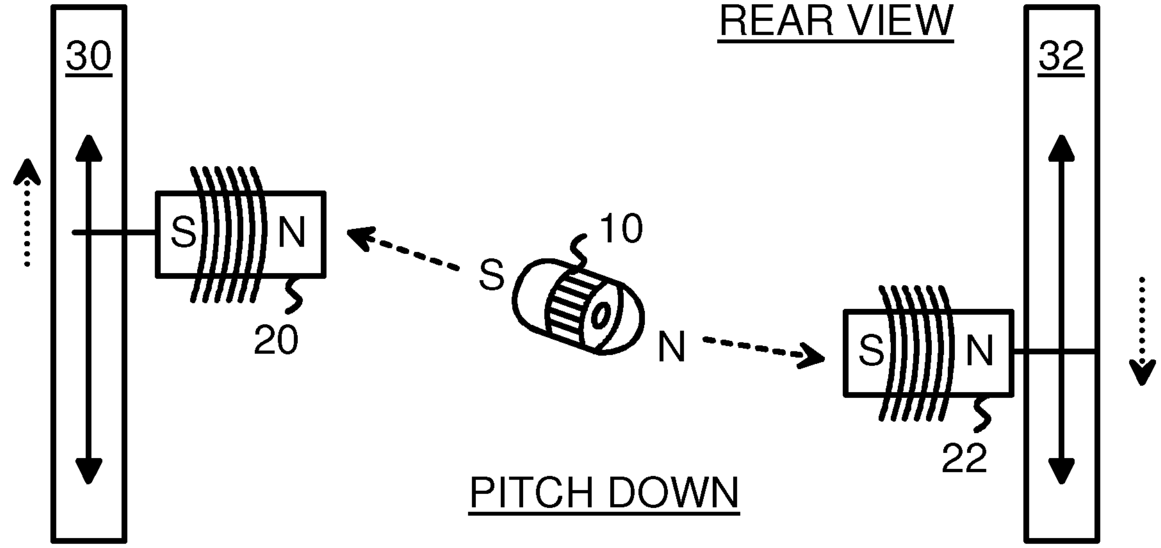
FIG. 11B
30
32
S
N
10
N
22
S
S
N
20
PITCH UP
Z
X
REAR VIEW
30
32
S
N
10
S
20
N
S
N
22
PITCH DOWN

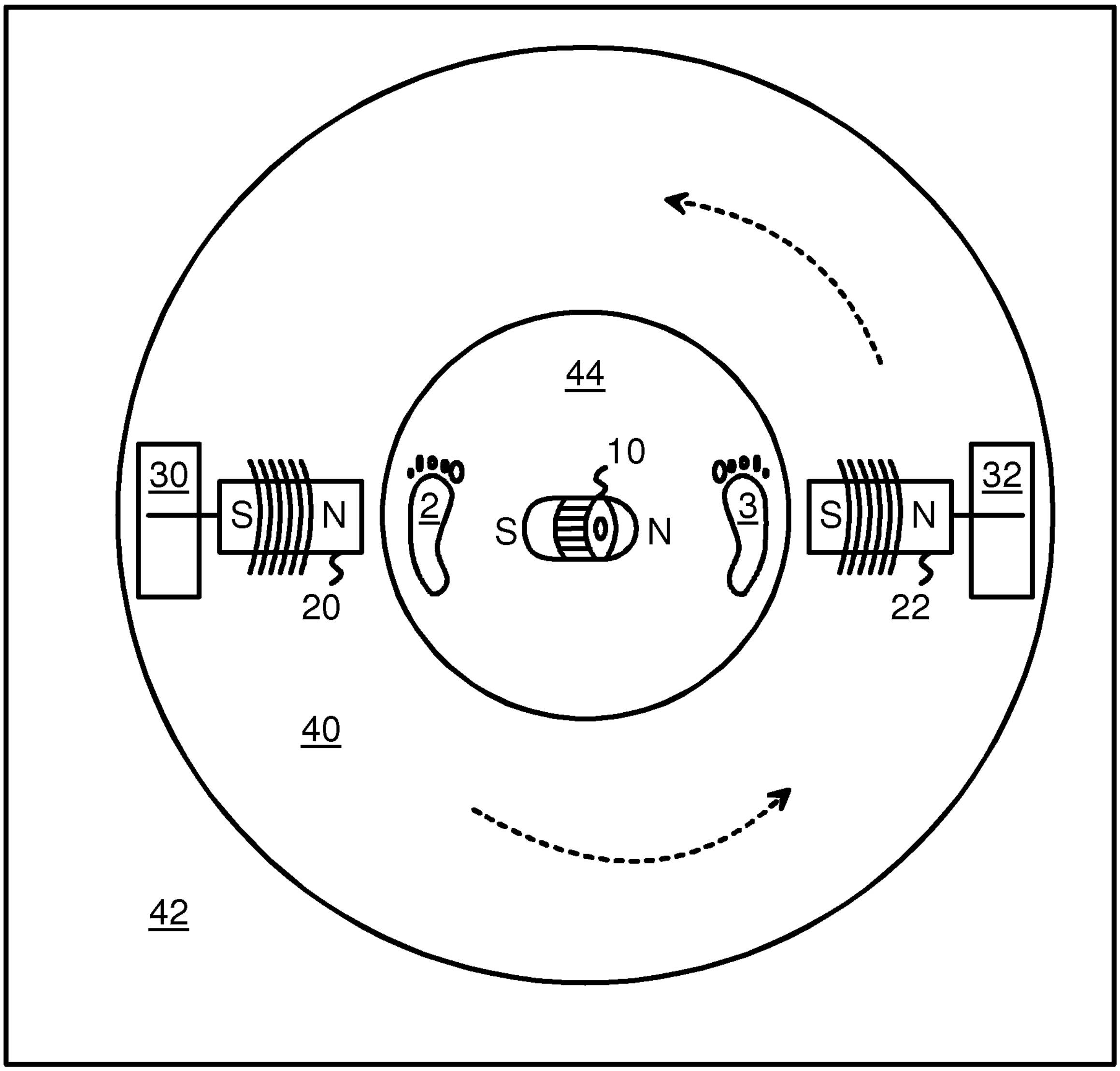
FIG. 12A
ROTATE
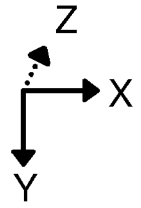
TOP VIEW

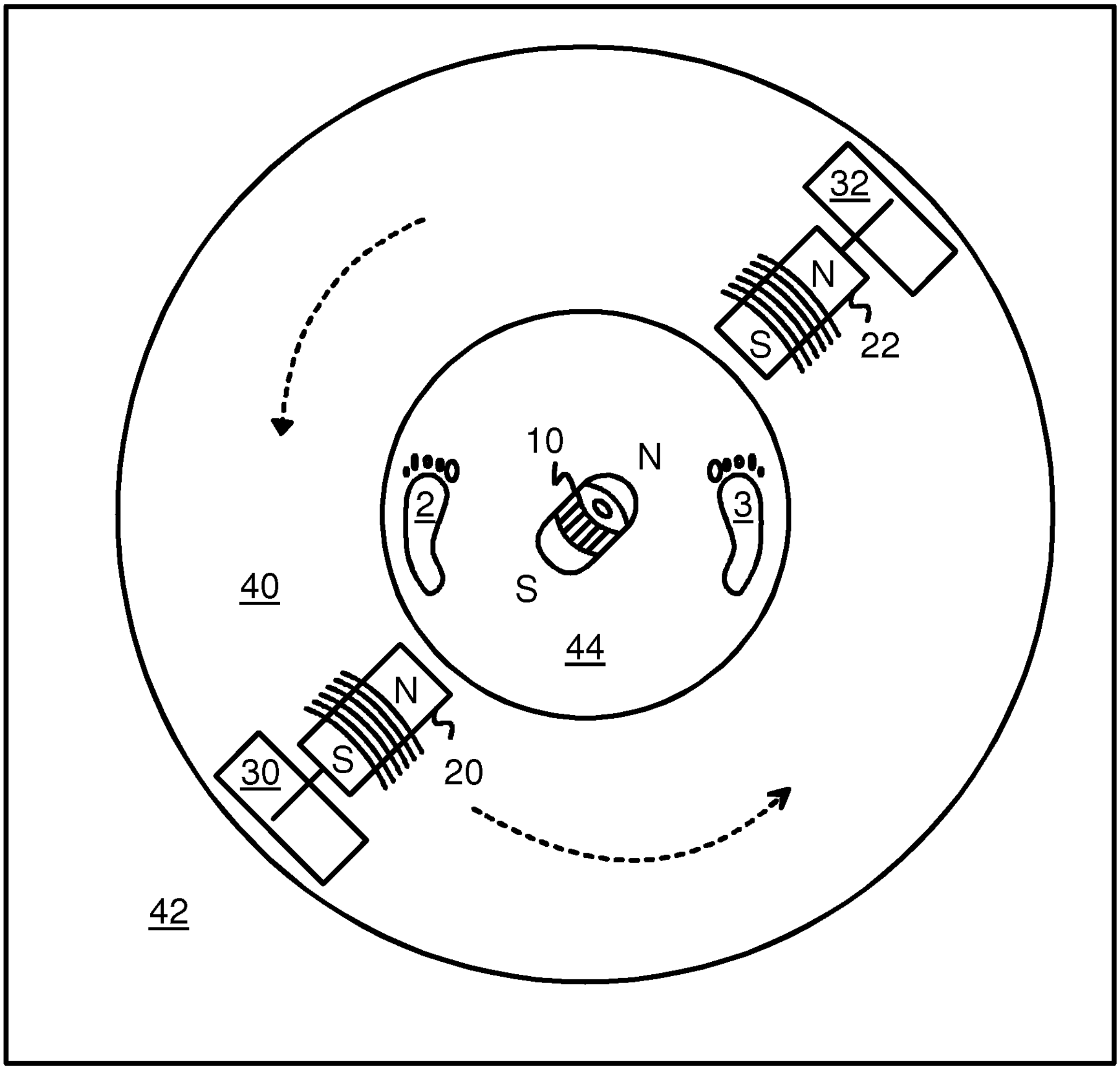
FIG. 12B
ROTATE
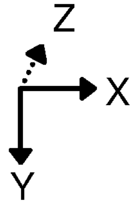
TOP VIEW

ROTATE

TOP VIEW

PORTABLE AUTOMATIC CONTROL SYSTEM FOR CAPSULE ENDOSCOPY IN STOMACH

FIELD OF THE INVENTION

This invention relates to medical screening devices, and more particularly to portable automatic screeners for capsule endoscopy of the stomach.

BACKGROUND OF THE INVENTION

Routine medical screenings can save lives as early detection before symptom onset can allow for an earlier diagnosis and intervention before disease progression. Colonoscopies are routinely performed every 10 years for certain age groups to screen entire populations for signs of cancer long before symptoms develop. Endoscopies likewise show promise for screenings for stomach problems.

FIG. 1 shows a prior-art endoscopy procedure. Patient 206 is sedated and lies on his side during the procedure, which may be performed in a medical office or outpatient clinic. During the procedure, doctor 202 manipulates gastroscope 208 to thread the end of the scope down the throat of sedated patient 206 to reach stomach 210. A light and camera attached to the end of gastroscope 208 allows doctor 202 to see images on display 204 as he manipulates gastroscope 208 to adjust the location and angle of this camera within stomach 210. Doctor 202 can more closely examine areas of stomach 210 with discoloration or other indications of disease, and then capture the images.

While useful, traditional endoscopy has several drawbacks. Skill is required to use gastroscope 208, so normally a specialist medical doctor is needed. Due to discomfort, the patient is usually sedated, which may cause dizziness and tiredness as sedation side effects. Endoscopy is not without risk. The famous celebrity Joan Rivers died during an endoscopy procedure in New York in 2014. Other risks include cross-infection due to reuse of gastroscope 208 among multiple patients, and bleeding caused by contact with gastroscope 208.

Traditional endoscopy is limited for use as a mass screening tool due to the cost, procedure time, and patient discomfort. Doctor 202 cannot be replaced by a less expensive technician due to the patient risk and skill needed to use gastroscope 208.

FIG. 2 shows a machine for magnetic capsule endoscopy. The patient swallows a small capsule that contains a camera, light source, battery, wireless transmitter, and magnet. The patient then lies on bed 222 while a doctor or technician operates magnetic endoscopy machine 220 to move the location and angle of the capsule in the patient's stomach using movable magnet 224 that is placed over the stomach. The doctor can see images 226 taken by the capsule that are sent wirelessly and displayed on the console's display.

The operator or doctor needs to be quick to examine the stomach, since the small size of the capsule limits the battery size and thus the length of time that the camera can operate. Also, magnetic endoscopy machine 220 can be very expensive and typically still requires a doctor to operate it. The size and bulk of magnetic endoscopy machine 220 inhibits its transport or portability. Since the patient lies flat on bed 222, the footprint of magnetic endoscopy machine 220 is quite large. Thus mass screenings are not practicable with magnetic endoscopy machine 220.

Mass screenings using capsule endoscopy are preferable to using gastroscope 208 since capsules are not reused so cross-contamination is avoided. The patient merely swallows the capsule, so sedation is avoided. The capsule is smooth and small so the danger of bleeding due to contact with gastroscope 208 is eliminated.

What is desired is mass screening using capsule endoscopy. A portable magnetic endoscopy machine is desired with a small footprint and that can be fitted into a box for transport. It is desired to perform endoscopy screenings in non-medical settings such as shopping malls so that more people will be screened, and to reduce cost. It is further desired to have automated computer control of the external magnets to position the magnetic capsule within the stomach to rapidly screen each stomach so that a smaller battery and capsule size are enabled. It is desired to automate capsule endoscopy so that a doctor is not required to operate the magnetic endoscopy machine, further cutting screening costs.

BRIEF DESCRIPTION OF THE DRAWINGS

FIGS. 11A-11B highlight angling capsule movement in the Z direction.

FIGS. 12A-12C highlight rotating magnets around the person.

DETAILED DESCRIPTION

The present invention relates to an improvement in magnetic endoscopy machines The following description is presented to enable one of ordinary skill in the art to make and use the invention as provided in the context of a particular application and its requirements. Various modifications to the preferred embodiment will be apparent to those with skill in the art, and the general principles defined herein may be applied to other embodiments. Therefore, the present invention is not intended to be limited to the particular embodiments shown and described but is to be accorded the widest scope consistent with the principles and novel features herein disclosed.

Figure 1:
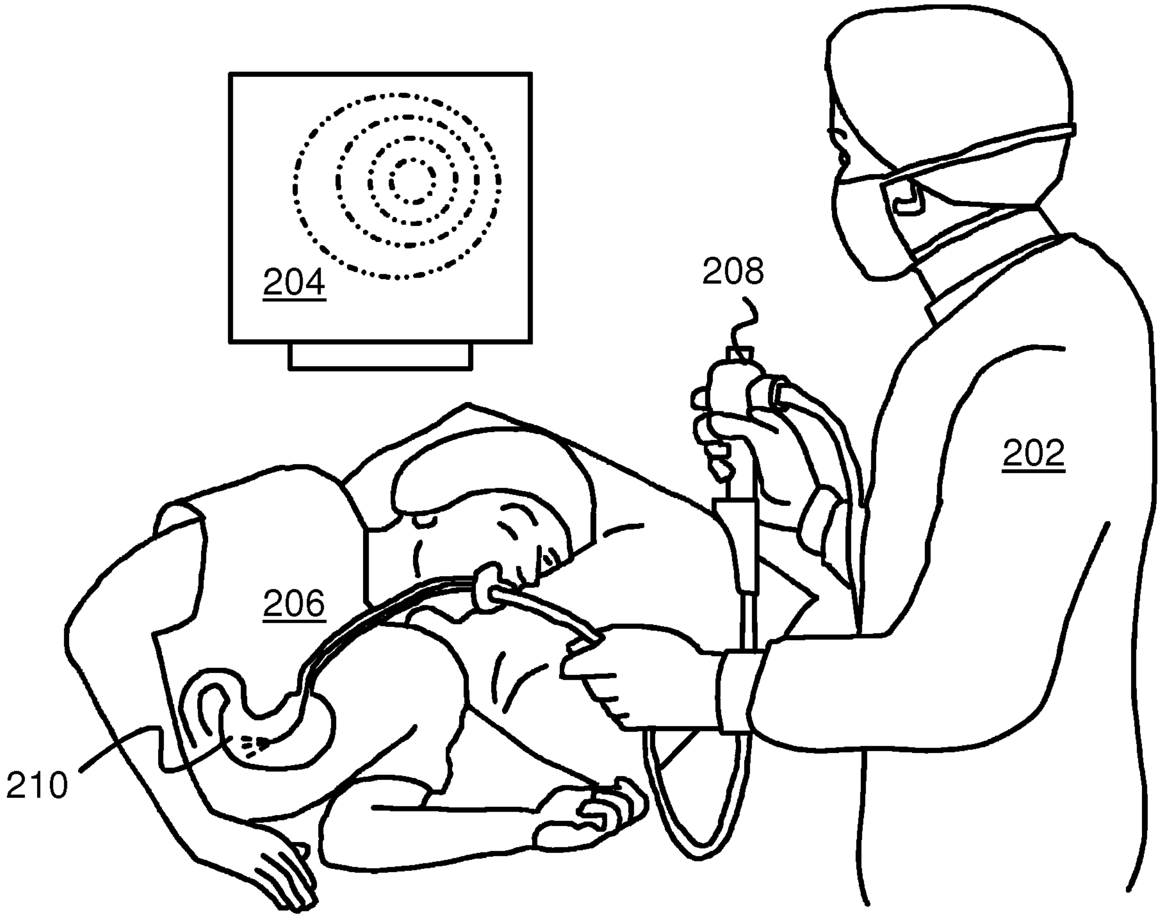
FIG. 1 shows a prior-art endoscopy procedure.
Figure 2:
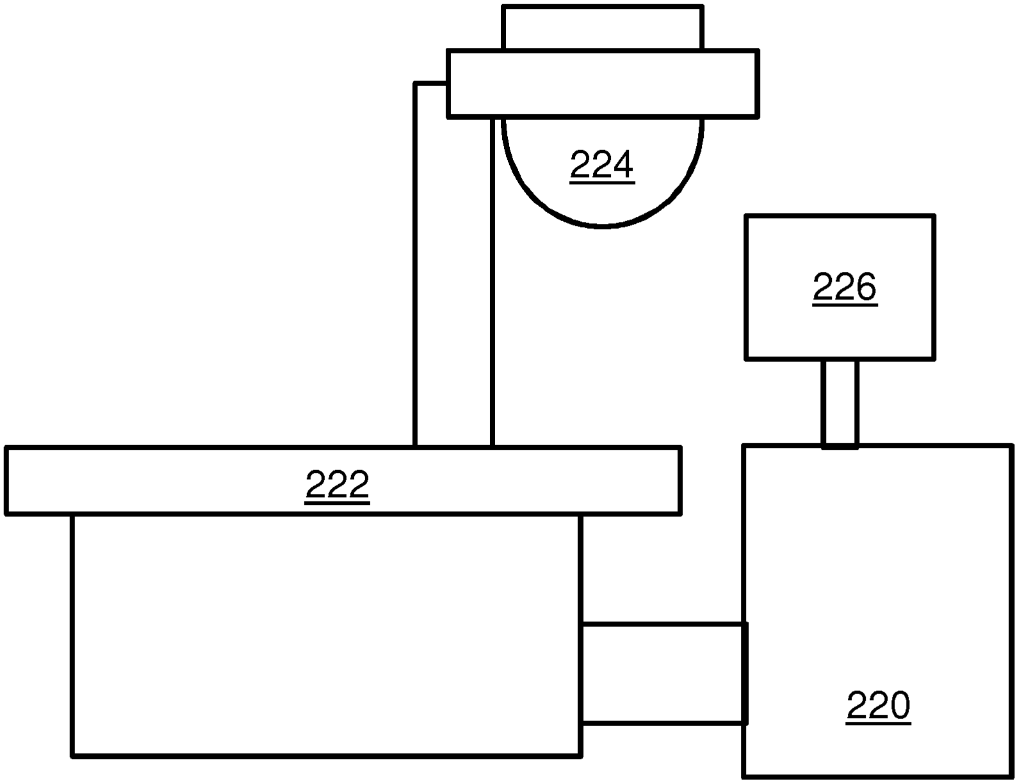
FIG. 2 shows a machine for magnetic capsule endoscopy.
Figure 3:
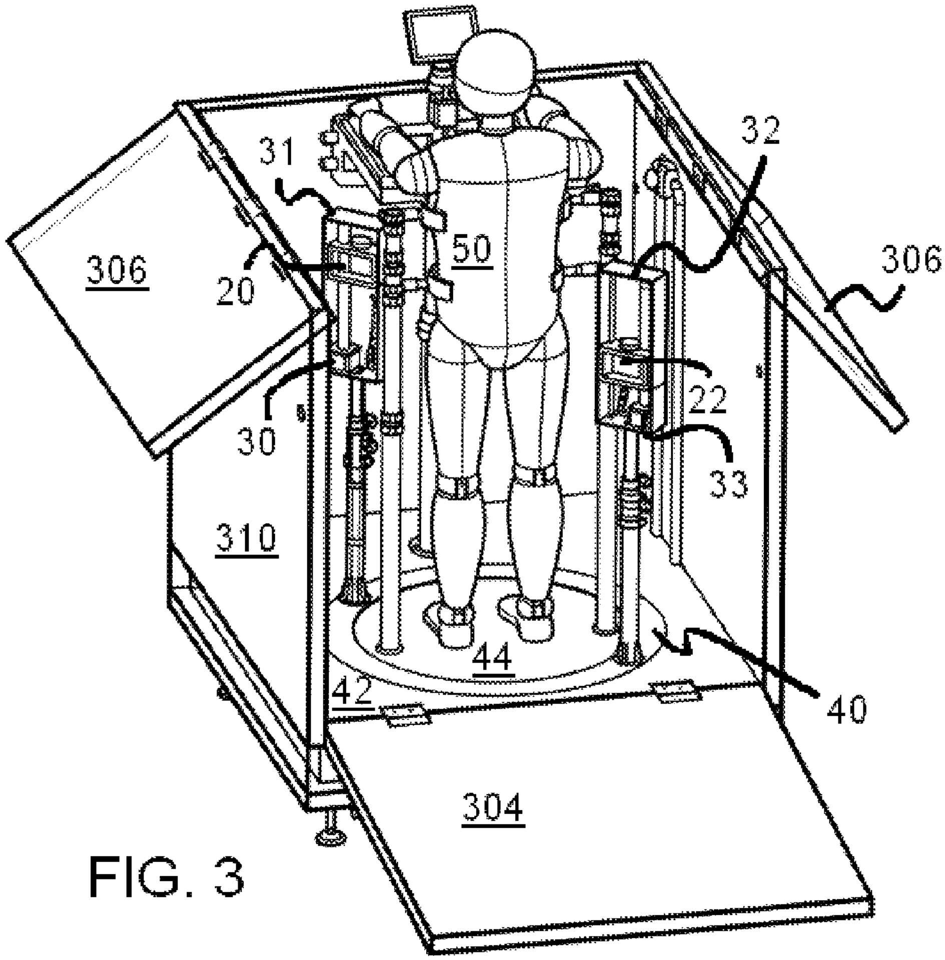
FIG. 3 shows an automated magnetic endoscopy machine in a box.

FIG. 3 shows an automated magnetic endoscopy machine in a box. Tops 306 of box 310 are flipped opened, and side 304 is lowered to permit person 50 to step into box 310 for screening. Person 50 stands on stationary disk 44 which is surrounded by rotating ring 40 on floor 42. Person 50 places his arms on stationary armrests and his stomach is held stationary by clamps that protrude from posts supported by stationary disk 44.

Left electromagnet assembly 31 is supported by a post that extends upward from rotating ring 40. Right electromagnet assembly 33 is likewise supported by another post that also extends upward from rotating ring 40. As rotating ring 40 rotates around stationary disk 44, left electromagnet assembly 31 and right electromagnet assembly 33 rotate around person 50. Electromagnet 20 inside left electromagnet assembly 31 is moved up and down by actuator 30 that is also inside left electromagnet assembly 31. Similarly, electromagnet 22 inside right electromagnet assembly 33 is moved up and down by actuator 32 that is also inside right electromagnet assembly 33.

Thus electromagnets 20, 22 are rotated around person 50 by rotating ring 40 so that the magnetic capsule inside the stomach of person 50 can be rotated to any radial angle in the full circle of rotating ring 40. Likewise actuators 30, 32 move electromagnets 20, 22 vertically to allow the magnetic capsule to be raised or lowered vertically within the stomach. Also, when electromagnet 20 is higher than electromagnet 22, as shown in FIG. 3, then the capsule can be angled up rather than be positioned within a horizontal plane, as will be shown later in FIG. 11B.

Figure 4:
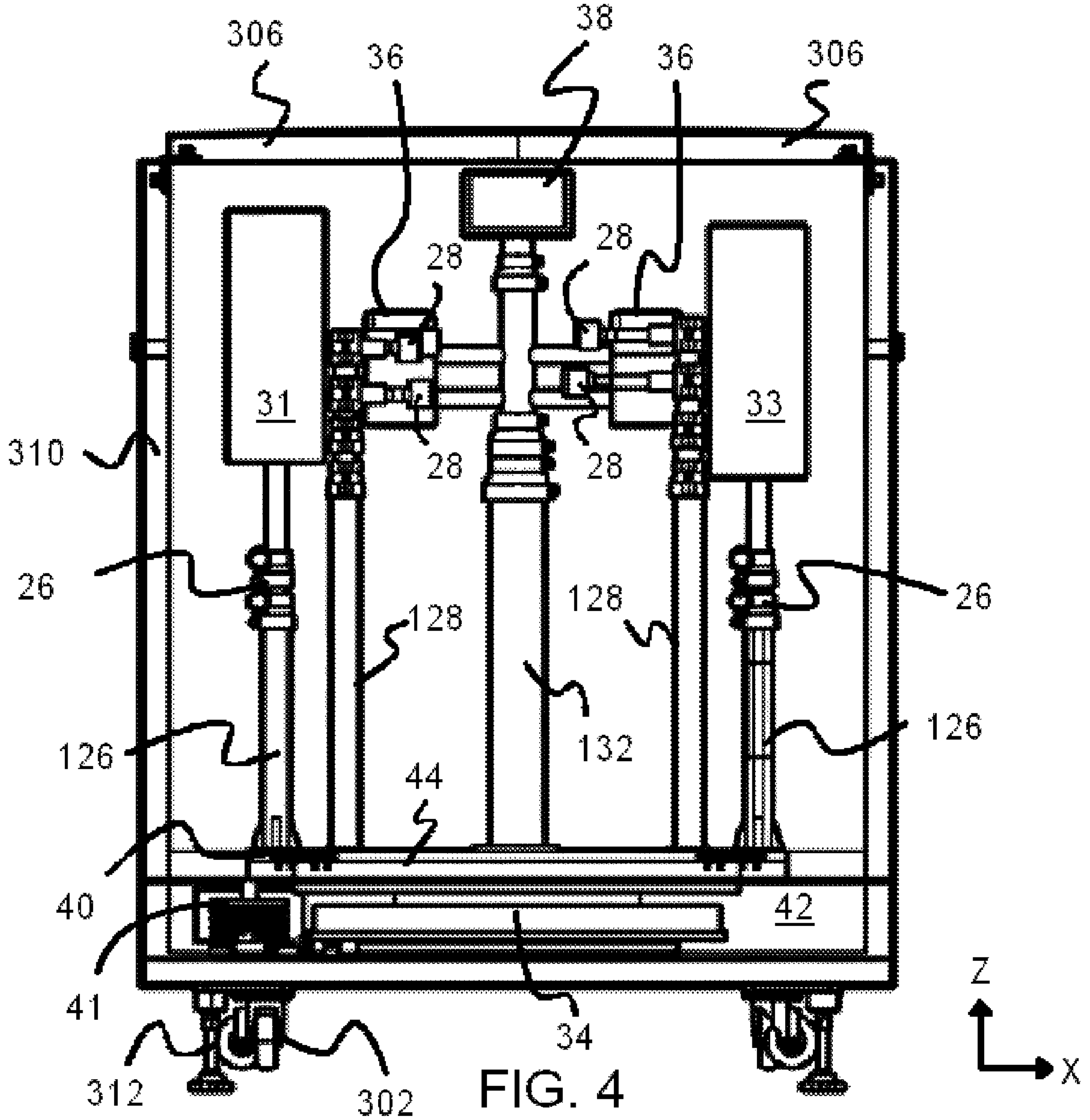
FIG. 4 is a rear cross-sectional view of the automated magnetic endoscopy machine with the box closed for transport.

FIG. 4 is a rear cross-sectional view of the automated magnetic endoscopy machine with the box closed for transport. Wheels 302 attached to the bottom of the box allow for easy transport of the automated magnetic endoscopy machine when supporting feet 312 are retracted. Tops 306 are closed over the top of box 310 and side 304 (not shown) is raised to cover the front.

Motor 41 has gears or other mechanisms to rotate rotating ring 40 around stationary disk 44 in floor 42. One post 126 is attached to rotating ring 40 and supports left electromagnet assembly 31, which can be manually adjusted in height by vertical adjustors 26. Another post 126 is also attached to rotating ring 40 and supports right electromagnet assembly 33, which likewise can be manually adjusted in height by vertical adjustors 26.

While posts 126 and left electromagnet assembly 31 and right electromagnet assembly 33 spin with rotating ring 40, fixed posts 128 is fixed to stationary disk 44 while front post 132 is fixed to floor 42. Thus fixed posts 128 and front post 132 do not move. Fixed posts 128 have clamps 28 that protrude inward to hold person 50 in place during screening. Front post 132 supports display 38 which can instruct person 50 to be still during the screening procedure or count down the time remaining or provide other information. Front post 132 also supports armrests 36 that person 50 places his arms on during the screening procedure.

Base electromagnet 34 is placed below stationary disk 44 under person 50. Base electromagnet 34 is normally de-energized and turned off but can be turned on to flip the magnet capsule, as is described later for FIG. 13. Base electromagnet 34 exerts a downward magnetic field in the vertical or Z direction. The vertical or Z direction and the left-right or X direction are shown in FIG. 4.

Figure 5:
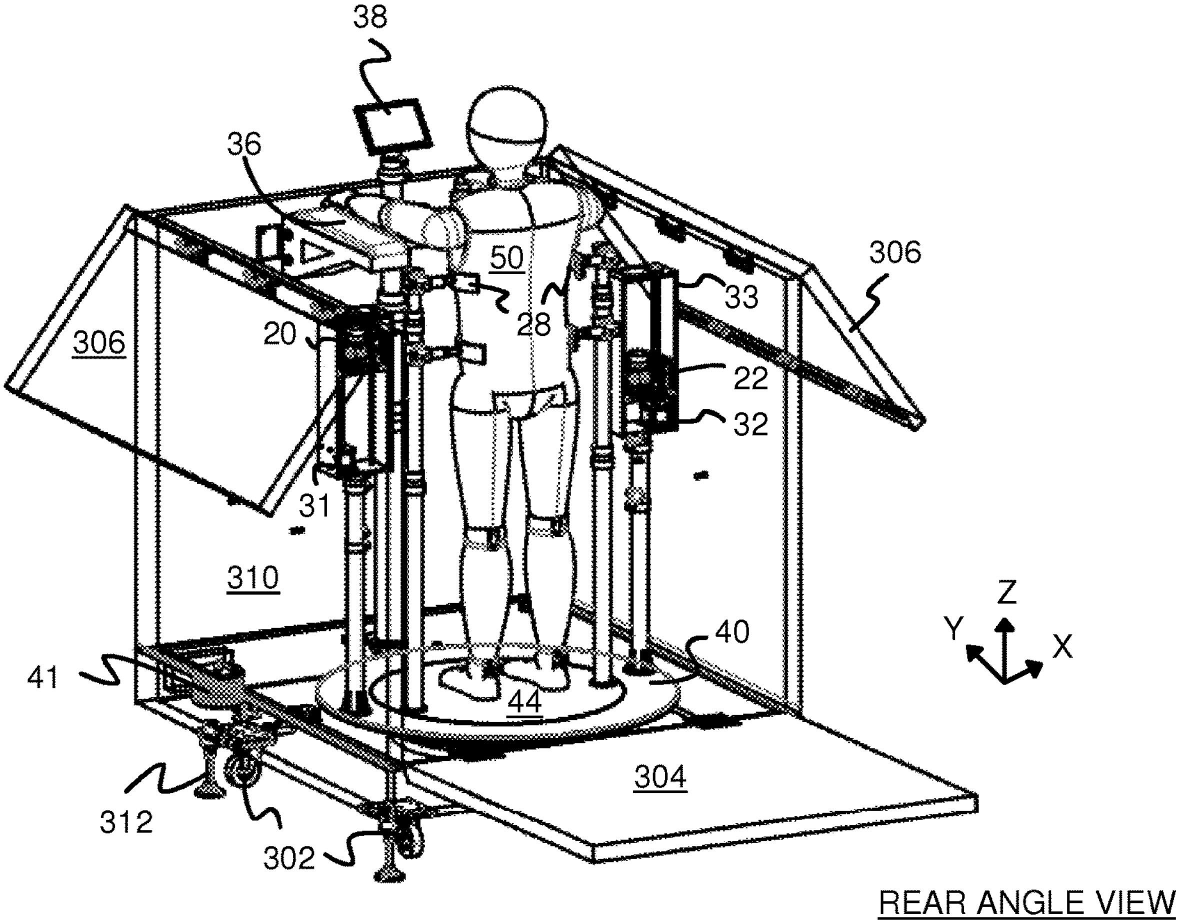
FIG. 5 shows a rear angle view of the automated magnetic endoscopy machine.

FIG. 5 shows a rear angle view of the automated magnetic endoscopy machine. The vertical or Z direction, the left-right or X direction, and the depth or Y direction are shown in FIG. 5.

Wheels 302 permit easy movement of box 310 but can be locked during screening to prevent movement. Legs 312 can be extended to support box 310 and prevent movement during screening. Hinges allow tops 306 and side 304 to be opened. Alternately, tops 306 and side 304 may be removable.

Person 50 steps into box 310 and stands on stationary disk 44. Clamps 28 can be manually adjusted to touch the sides of person 50 to prevent movement of the stomach area. Person 50 places his arms on armrests 36 and reads any instruction on display 38. Display 38 can be extended upward by telescoping extensions on front post 132 for better viewing.

During the automated procedure, a computer within box 310 that controls display 38 activates motor 41 to rotate rotating ring 40 and thus rotate electromagnets 20, 22 around person 50 in a testing sequence as the magnetic capsule and its camera are forced into different angles in the X-Y plane. Actuators 30, 32 are activated by the computer to vertically adjust electromagnets 20, 22 in the Z axis. Thus X, Y, Z control of the magnetic capsule are provided.

Figure 6:
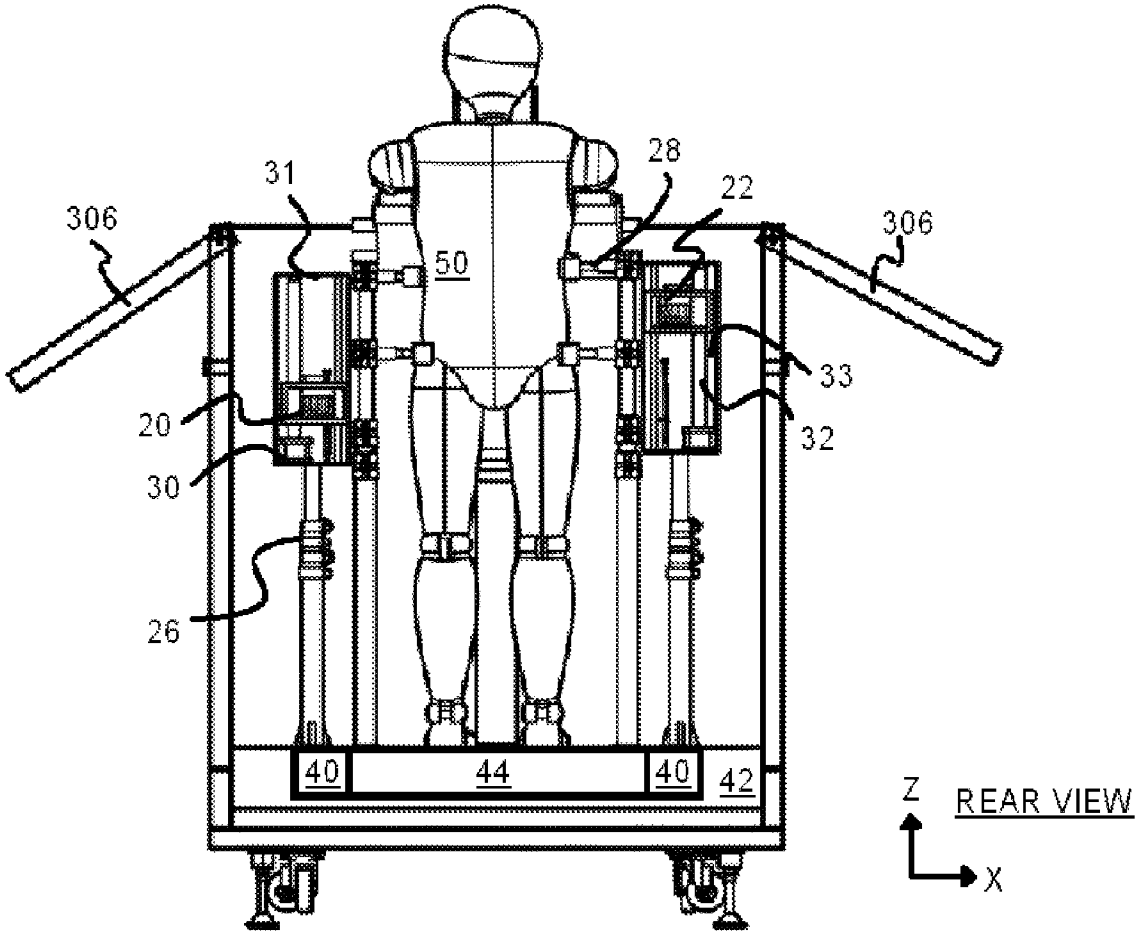
FIG. 6 is a rear view of the automated magnetic endoscopy machine.

FIG. 6 is a rear view of the automated magnetic endoscopy machine. Tops 306 are opened and person 50 stands on stationary disk 44 that is fixed to floor 42. Clamps 28 prevent person 50 from moving his stomach during testing.

Rotating ring 40 rotates around stationary disk 44 during testing, rotating left electromagnet assembly 31 and right electromagnet assembly 33 around stationary person 50. Telescoping poles and clamps for vertical adjustors 26 can permit left electromagnet assembly 31 and right electromagnet assembly 33 to be manually adjusted vertically for the height of person 50 before testing begins. During testing, the computer controls actuator 30 to move electromagnet 20 up and down within left electromagnet assembly 31, and controls actuator 32 to move electromagnet 22 up and down (Z) within right electromagnet assembly 33.

In FIG. 6, electromagnet 20 is lower in the vertical or Z direction and electromagnet 22 is higher in the Z direction. This positioning causes the magnetic capsule to be positioned at an angle to the horizontal X-Y plane, permitting the capsule camera to take images out of the X-Y plane, upward to the right of person 50.

Figure 7:
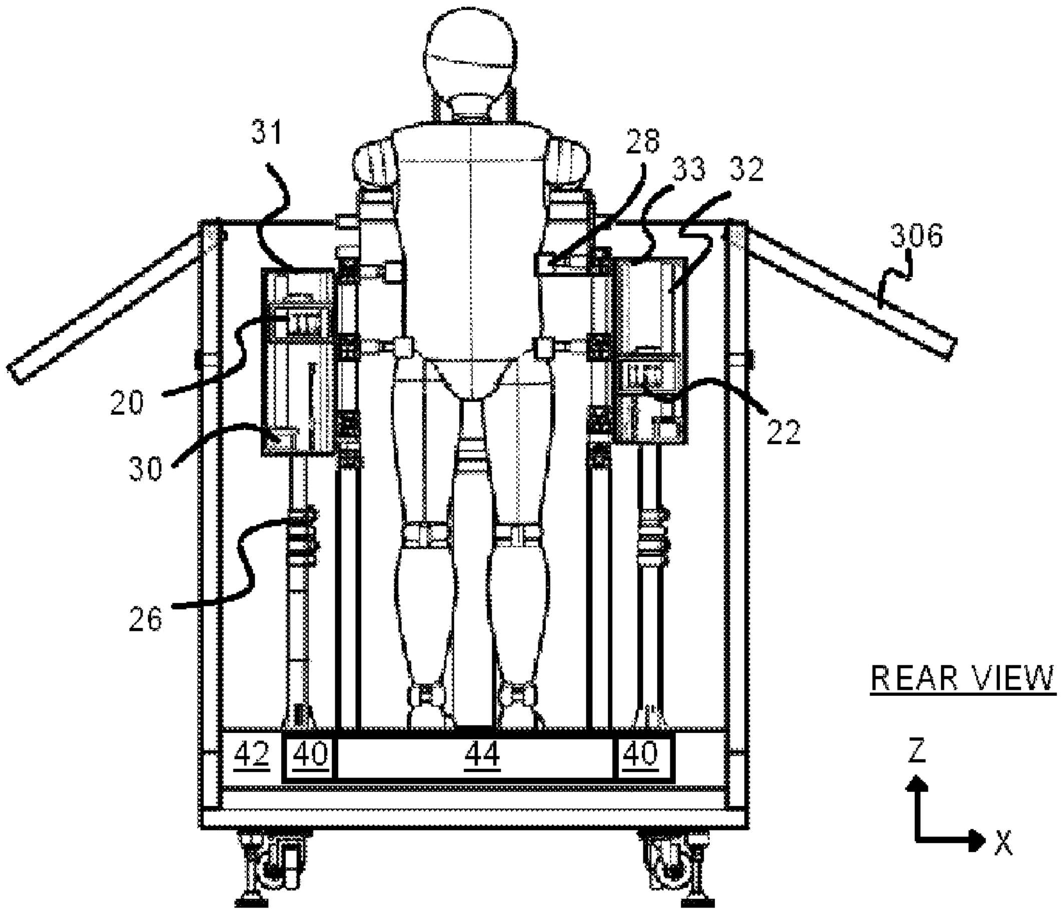
FIG. 7 is a rear view of the automated magnetic endoscopy machine highlighting angled electromagnet placement for angled capsule imaging.

FIG. 7 is a rear view of the automated magnetic endoscopy machine highlighting angled electromagnet placement for angled capsule imaging. In FIG. 7, electromagnet 20 is higher in the vertical or Z direction and electromagnet 22 is lower in the Z direction. This positioning causes the magnetic capsule to be positioned at a different angle to the horizontal X-Y plane, permitting the capsule camera to take images out of the X-Y plane, downward to the right of person 50.

Figure 8:
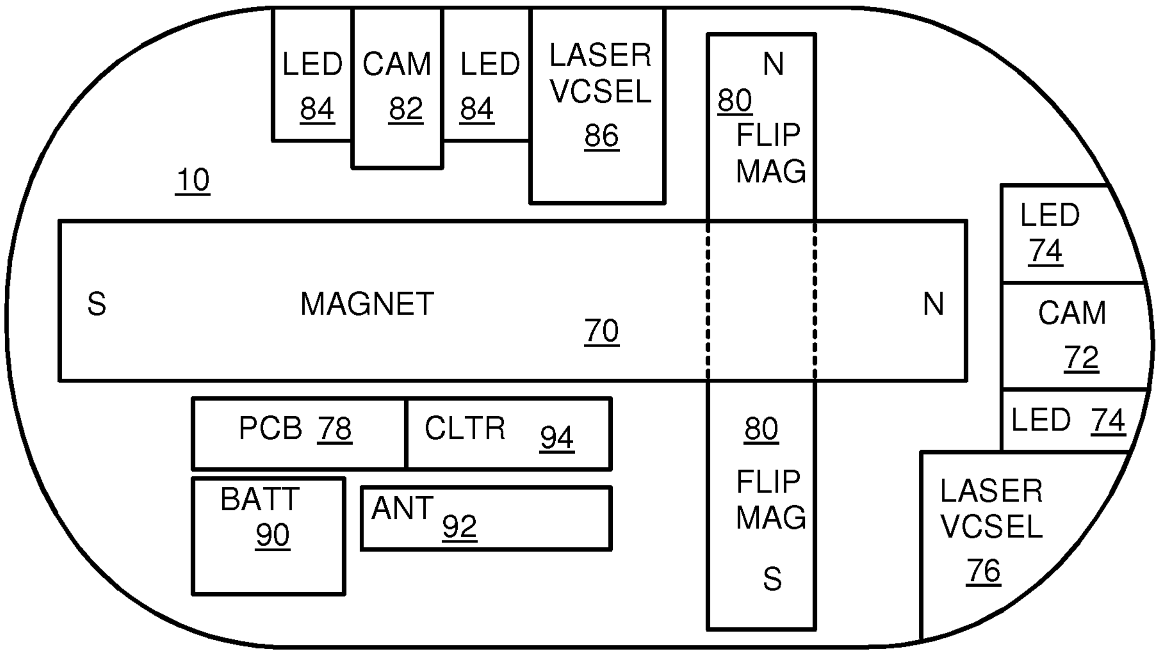
FIG. 8 is a diagram of the magnetic capsule.

FIG. 8 is a diagram of the magnetic capsule. Capsule 10 is relatively small and is swallowed by the person just before screening. Capsule 10 can first be activated or woken up before being handed to the person so that battery 90 does not get depleted before the screening starts.

Capsule 10 executes programs on controller 94 that is mounted to Printed Circuit Board (PCB) 78 that connects power from battery 90 to controller 94 and to other components on or off PCB 78 such as cameras 72, 82 and their Light Emitting Diodes (LED) 74, 84, and lasers 76, 86.

Lasers 76, 86 each can be a Vertical-Cavity Surface-Emitting Laser (VCSEL) that are used to generate laser beams that are bounced off the walls of the stomach. The returned laser beams are then detected to determine the range or distance to the stomach walls. The physical shape of the stomach can then be mapped out by lasers 76, 86 before image capture by cameras 72, 82.

The tip or end of capsule 10 is provided with laser 76, camera 72, and its LED's 74, to permit laser distance-measurement and image capture from the front end of capsule 10. The longer side of capsule 10 is also fitted with laser 86, camera 82, and its LEDs 84 to permit laser distance-measurement and image capture from the side of capsule 10. LEDs 74 provide front-facing illumination for images captured by front camera 72, while LEDs 84 provide side-facing illumination for images captured by side camera 82.

Cameras 72, 82 and lasers 76, 86 are oriented within the stomach using external electromagnets 20, 22 to move capsule 10 through a magnetic force applied to primary magnet 70. During screening, actuators 30, 32 and rotating ring 40 move to change the magnetic field orientation and thus change the orientation of capsule 10 to capture different images within the stomach. A sequence of such movements is programmed into an automatic screening routine so that images of the entire stomach can be quickly captured.

Primary magnet 70 and flip magnet 80 are permanent magnets that are mounted at right angles to each other. Primary magnet 70 is larger and has a higher magnetic strength than flip magnet 80. When electromagnets 20, 22 (FIGS. 3-7) are energized, they exert a greater force on primary magnet 70 than on flip magnet 80 so that capsule 10 moves to align primary magnet 70 with the external magnetic field generated by electromagnets 20, 22.

During screening, after images from the upper half of the stomach are captured by camera 82 facing upward, capsule 10 can be flipped over to cause camera 82 to face downward so that the lower half of the stomach can be imaged by camera 82. Base electromagnet 34 (FIG. 4, 13) is activated when capsule 10 is in or near the X-Y plane. Base electromagnet 34 is then nearly parallel to primary magnet 70 so that only small net force is applied to primary magnet 70 from base electromagnet 34. Thus base electromagnet 34 exerts a magnetic force mostly on flip magnet 80, not as much on primary magnet 70. This force on flip magnet 80 causes capsule 10 to rotate along the longitudinal axis parallel to primary magnet 70, flipping camera 82 to face downward rather than upward.

Images captured by cameras 72, 82 are sent to controller 94 or its memory (not shown) and are then wirelessly transmitted by antenna 92 to a wireless transceiver on the automated magnetic endoscopy machine. The received images can then be stored and analyzed by the automated screening program. When abnormalities are detected, such as dark colored spots on the stomach wall, then the program can instruct actuators 30, 32, and rotating ring 40 to orient capsule 10 to point a camera at the location of the abnormality so that further images may be captured. The program may also move capsule 10 closer to the abnormality such as by increasing power to electromagnet 20 or to electromagnet 22 until capsule 10 is in the desired location for close-up image capture.

Figure 9A:
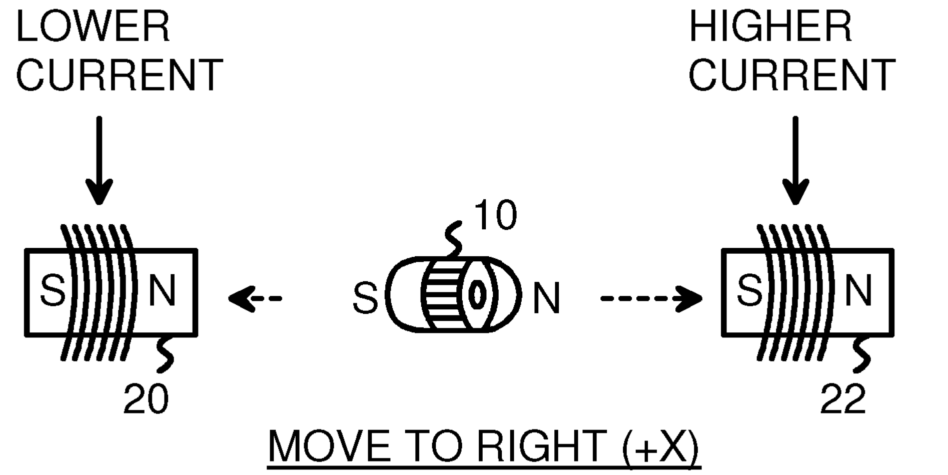
FIGS. 9A-9B highlight capsule movement in the X direction.
Figure 9B:
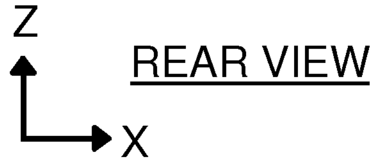
Figure 9B:
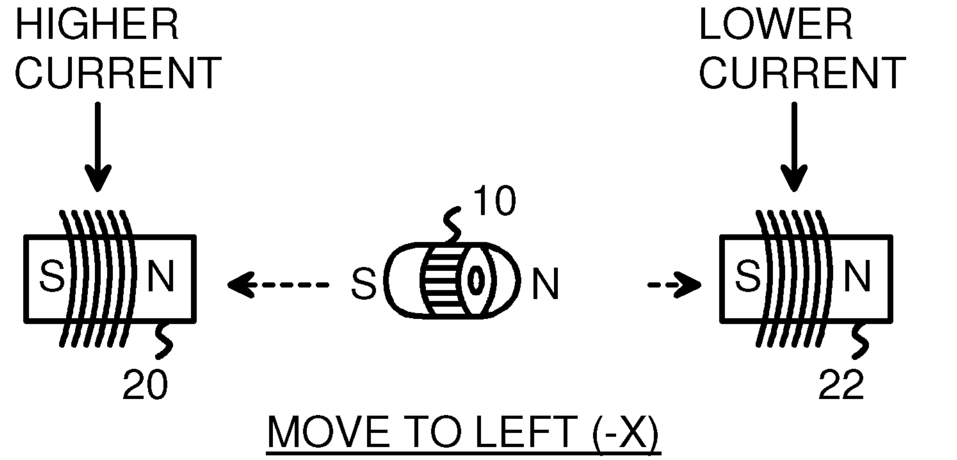

FIGS. 9A-9B highlight capsule movement in the X direction. In FIG. 9A, capsule 10 is inside the stomach of person 50 with electromagnet 20 to his left and electromagnet 22 to his right, and both electromagnets 20, 22 at the same Z position. When the automated program instructs the automated magnetic endoscopy machine to increase electrical current to electromagnet 22 and to decrease electrical current to electromagnet 20, then electromagnet 22 exerts a larger force on capsule 10 than does electromagnet 20, and capsule 10 is pulled to the right, toward electromagnet 22. Thus the automated program can move capsule 10 in the +X direction.

In FIG. 9B, the automated program is applying higher current to electromagnet 20 and less current to electromagnet 22, so that electromagnet 20 exerts a higher force. Capsule 10 moves toward electromagnet 20 within the confines of the stomach. The automated program may apply the increased current for only a short period of time that is sufficient to move capsule 10 the desired amount, or may remain on to hold capsule 10 stationary once it reaches a location that balances the forces of electromagnets 20, 22. The control program may calculate the period of time of acceleration or deceleration of capsule 10 to calculate the distance moved. Thus the automated program also can move capsule 10 in the −X direction.

Figure 10A:
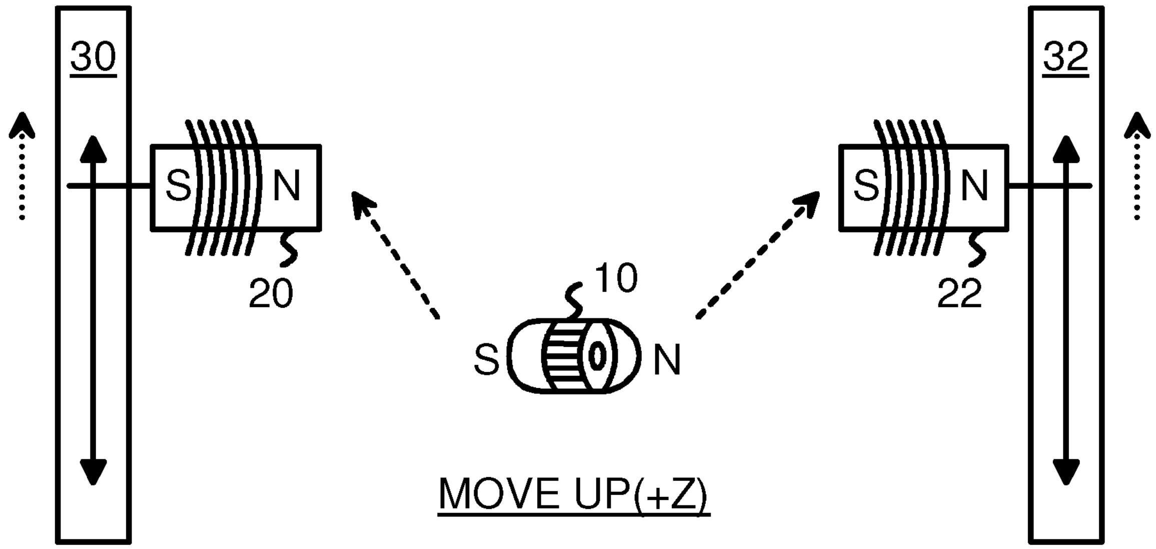
FIGS. 10A-10B highlight capsule movement in the Z direction.
Figure 10B:
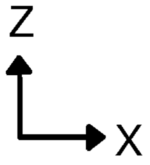
Figure 10B:
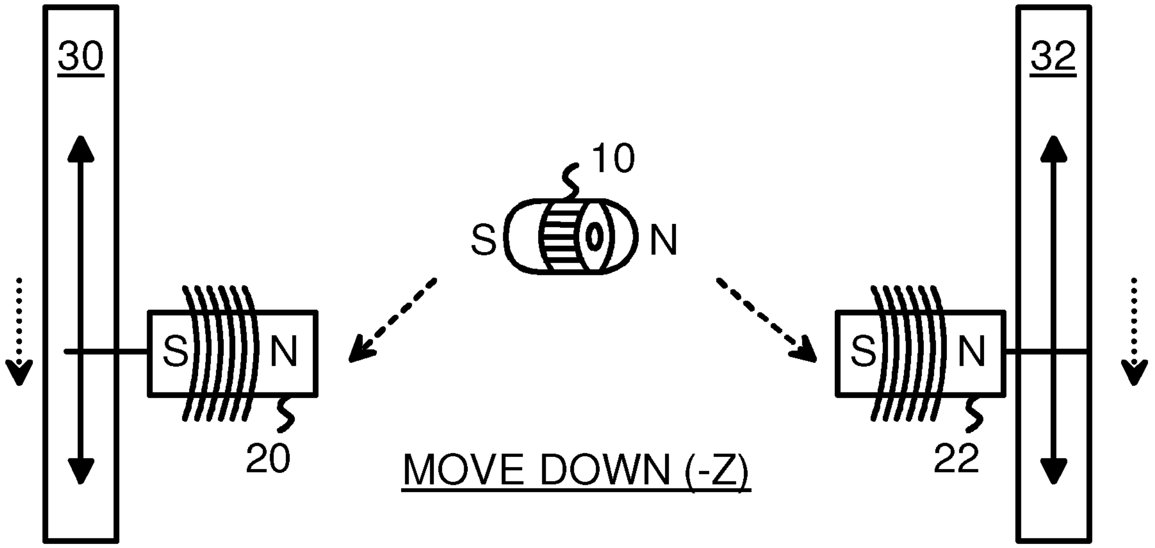

FIGS. 10A-10B highlight capsule movement in the Z direction. In FIG. 10A, capsule 10 is inside the stomach of person 50 with electromagnet 20 to his left and electromagnet 22 to his right, and both electromagnets 20, 22 at the same Z position.

When the automated program intends to move capsule 10 upward in the +Z direction, the program activates actuator 30 to move electromagnet 20 upward, such as along a mechanical track. The amount of upward movement can be a number of teeth in the track, or can be a period of time that actuator 30 is activated that corresponds to a physical amount of Z movement. The program also activates actuator 32 to move right electromagnet 22 upward, such as by the same amount as left electromagnet 20.

Current can be applied to electromagnets 20, 22, either after the Z movement of actuators 30, 32 have been completed, or during this actuator Z movement. Then primary magnet 70 inside capsule 10 is attracted to electromagnets 20, 22, and this magnetic attraction pulls capsule 10 upward in the +Z direction, until capsule 10 is in the same horizontal or X-Y plane as electromagnets 20, 22.

In FIG. 10B, the automated program intends to move capsule 10 downward in the −Z direction. The program activates actuator 30 to move electromagnet 20 downward, such as along a mechanical track. The program also activates actuator 32 to move right electromagnet 22 downward, such as by the same amount as left electromagnet 20.

Current can be applied to electromagnets 20, 22, either after the Z movement of actuators 30, 32 have been completed, or during this actuator Z movement. Then primary magnet 70 inside capsule 10 is attracted to electromagnets 20, 22, and this magnetic attraction pulls capsule 10 downward in the +Z direction, until capsule 10 is in the same horizontal plane as electromagnets 20, 22.

FIGS. 11A-11B highlight angling capsule movement in the Z direction. Front camera 72 faces forward, such as toward right electromagnet 22. The automated program may desire to capture an image that is above the horizontal X-Y plane of capsule 10. The program could move capsule 10 upward, such as shown in FIG. 10A, but near the top of the stomach there may be insufficient space within the stomach to do that.

In FIG. 11A, the automated program pitches up capsule 10 so that its front-facing camera 72 can image the upper corner walls of the stomach. The automated program activates actuator 30 to move electromagnet 20 downward, such as along a mechanical track. The program also activates actuator 32 to move right electromagnet 22 upward, in the opposite Z direction as left electromagnet 20.

Current can be applied to electromagnets 20, 22, either after the Z movement of actuators 30, 32 have been completed, or during this actuator Z movement. Then primary magnet 70 inside capsule 10 is attracted to electromagnets 20, 22, and this magnetic attraction pitches capsule 10 upward and to the right, until capsule 10 is in an angled plane through electromagnets 20, 22.

In FIG. 11B, the automated program pitches down capsule 10 so that its front-facing camera 72 can image the lower corner walls of the stomach. The automated program activates actuator 30 to move electromagnet 20 upward, such as along a mechanical track. The program also activates actuator 32 to move right electromagnet 22 downward, in the opposite Z direction as left electromagnet 20.

Current can be applied to electromagnets 20, 22, either after the Z movement of actuators 30, 32 have been completed, or during this actuator Z movement. Then primary magnet 70 inside capsule 10 is attracted to electromagnets 20, 22, and this magnetic attraction pitches capsule 10 downward and to the right, until capsule 10 is in an angled plane through electromagnets 20, 22. The lower part of the stomach wall can then be imaged using front-facing camera 72.

Figure 12C:
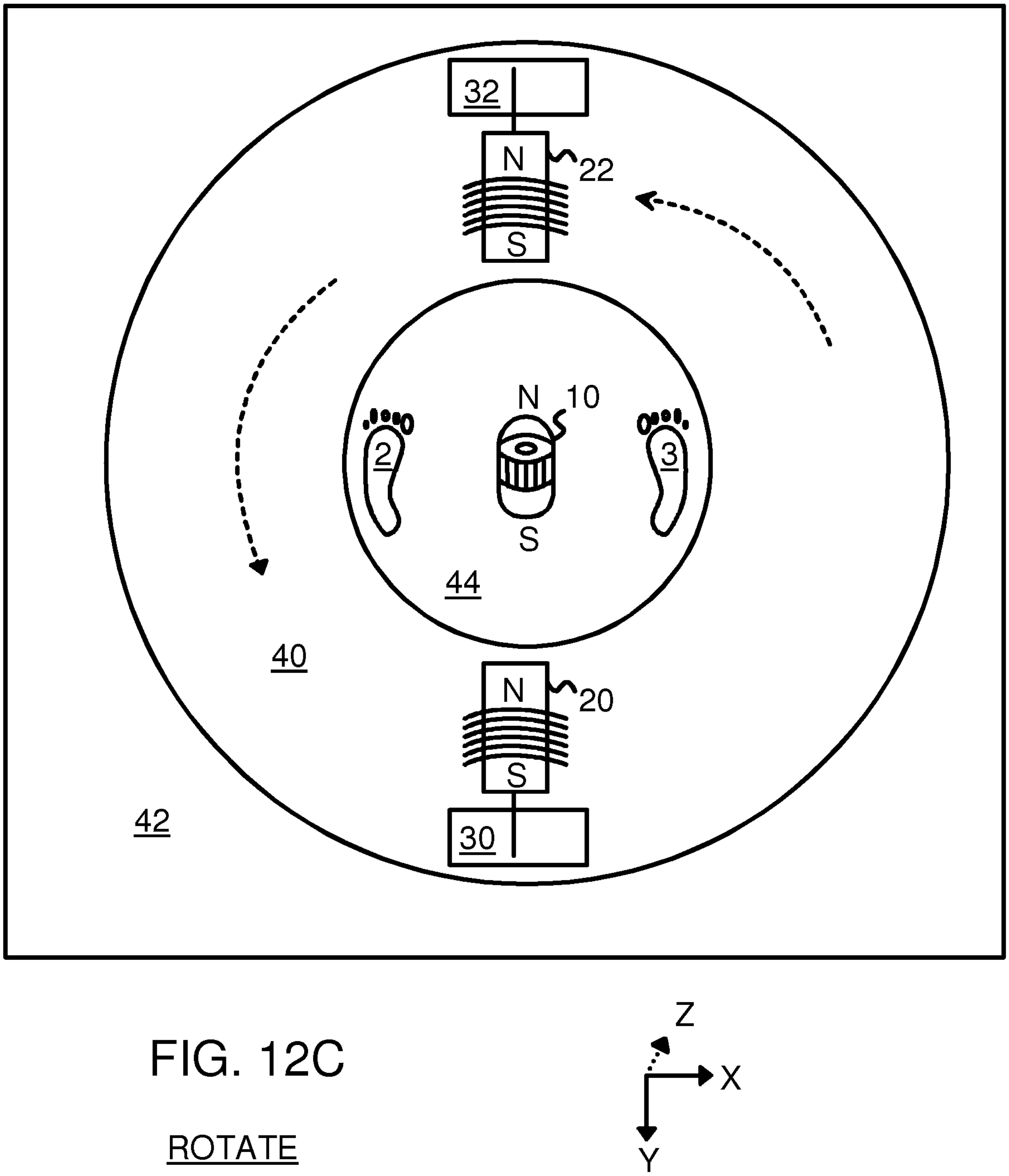

FIGS. 12A-12C highlight rotating magnets around the person. In FIG. 12A, an overhead or top view has person 50 (not shown) standing on stationary disk 44 so that his feet 2, 3 are shown on stationary disk 44, and capsule 10 inside his stomach is between his feet 2, 3, but in a higher plane in the Z direction.

The automated program can rotate rotating ring 40 around stationary disk 44 by activating motor 41 (FIG. 4). Left electromagnet 20 can be moved in the Z direction by actuator 30, which is within left electromagnet assembly 31 (FIG. 3) that is mounted to rotating ring 40 by left fixed post 128 (FIG. 4). Similarly, right electromagnet 22 can be moved in the Z direction by actuator 32, which is within right electromagnet assembly 33 (FIG. 3) that is mounted to rotating ring 40 by right fixed post 128 (FIG. 4). Floor 42 and stationary disk 44 are stationary while rotating ring 40 rotates.

In FIG. 12A, electromagnet 20 is to the person's left, and electromagnet 22 is to the person's right, and capsule 10 is aligned to electromagnets 20, 22 in a default radial plane with rotating ring 40 not having been rotated. The default radial plane is a vertical plane passing through the person, from head to feet, and includes his stomach and capsule 10.

In FIG. 12B, the automated program has activated motor 41 to rotate rotating ring 40 counterclockwise by about 45 degrees. Rotation occurs around a vertical rotational axis that is at the center of stationary disk 44, and typically passes through the person's head and lower stomach. Electromagnet 20 is now to the person's back left, and electromagnet 22 is to the person's front right. Capsule 10 rotates within the stomach to align to electromagnets 20, 22.

Capsule 10 falls within a 45-degree radial plane after rotating ring 40 was rotated 45 degrees. This 45-degree radial plane includes capsule 10 and electromagnets 20, 22, as well as the person's stomach and head. Front-facing camera 72 inside capsule 10 can capture images of the front-right walls of the stomach. Side-facing camera 82 that is also inside capsule 10 can capture images of the upper-left walls of the stomach.

In FIG. 12C, the automated program has activated motor 41 to rotate rotating ring 40 counterclockwise by about 90 degrees. Electromagnet 20 is now to the person's back, and electromagnet 22 is to the person's front. Capsule 10 rotates within the stomach to align to electromagnets 20, 22.

Capsule 10 falls within a 90-degree radial plane after rotating ring 40 was rotated 90 degrees. This 90-degree radial plane includes the vertical rotational axis through the center of stationary disk 44. The radial plane passes through capsule 10 and electromagnets 20, 22, as well as the person's stomach and head, and slices the person into right and left halves down his centerline.

Front-facing camera 72 inside capsule 10 can capture images of the front walls of the stomach. Side-facing camera 82 that is also inside capsule 10 can capture images of the top walls of the stomach.

Rotating ring 40 could be further rotated, or rotated clockwise rather than counterclockwise, to align electromagnets 20, 22 and capsule 10 to any radial plane or rotated plane. For example, rotating ring 40 could be rotated clockwise by 270 degrees so that electromagnet 20 is to the person's front and electromagnet 22 is to the person's back, to allow front-facing camera 72 to image the back walls of the stomach.

Thus rotating ring 40 allows all 360 degrees of the stomach wall to be imaged by capsule 10. Capsule 10 and its cameras can be rotated through all 360 degrees using electromagnets 20, 22 attached to rotating ring 40.

Figure 13:
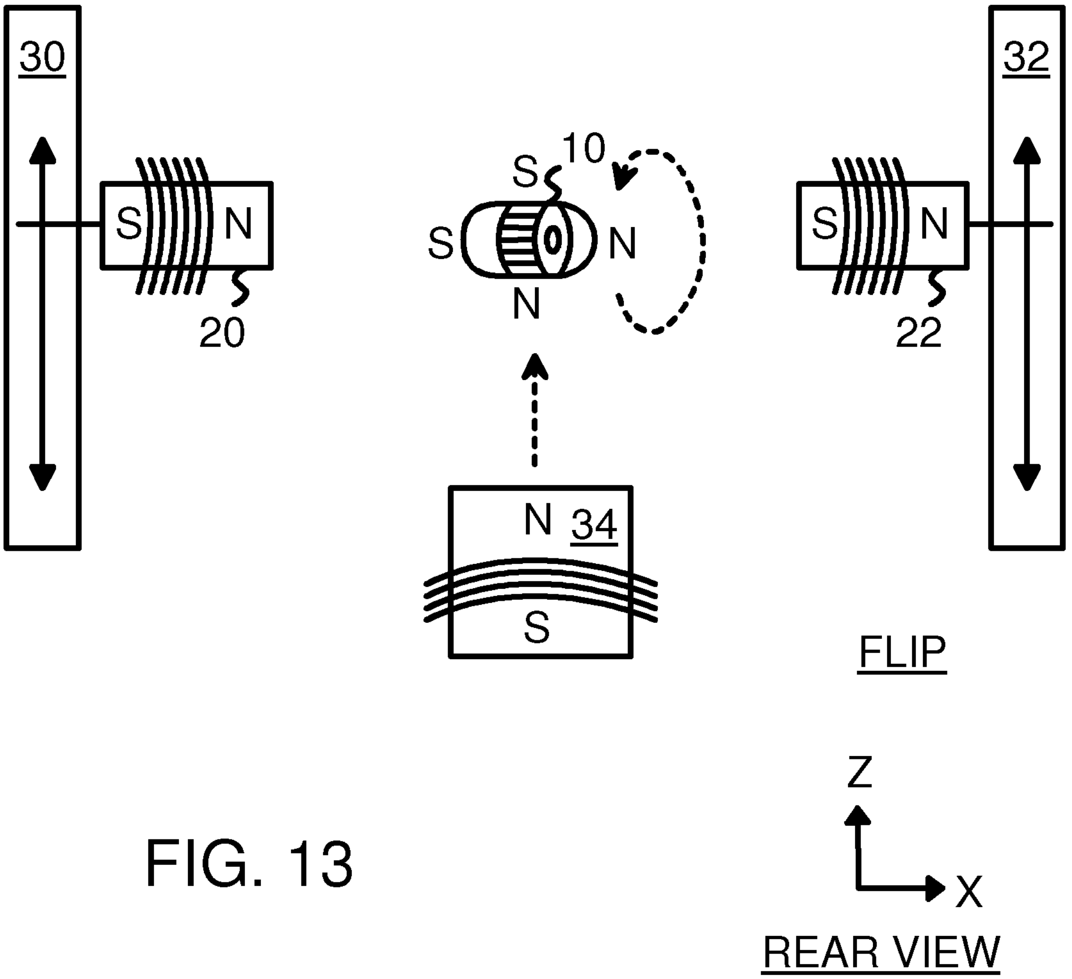
FIG. 13 highlights flipping the capsule using the base magnet under the person's feet.

FIG. 13 highlights flipping the capsule using the base magnet under the person's feet. During screening, after images from the upper half of the stomach are captured by side camera 82 facing upward, capsule 10 can be flipped over to cause side camera 82 to face downward so that the lower half of the stomach can be imaged by side camera 82.

Base electromagnet 34 (FIG. 4) is activated when capsule 10 is close to the X-Y plane and is not pitched up or down by a large amount (FIG. 11A-11B). Actuators 30, 32 may be placed in the same or nearly same Z location or setting so that electromagnet 20 and electromagnet 22 are in the same X-Y plane parallel to floor 42 or are pitched only slightly.

Base electromagnet 34 is then nearly parallel to primary magnet 70 so that only a small net force is applied to primary magnet 70 from base electromagnet 34. Thus base electromagnet 34 exerts a magnetic force mostly on flip magnet 80, not as much on primary magnet 70.

When the automated program activates base electromagnet 34, the force exerted by base electromagnet 34 onto flip magnet 80 causes capsule 10 to rotate along the longitudinal axis parallel to primary magnet 70, flipping side camera 82 to face downward rather than upward.

The flip force required is relatively small since the rotational motion of capsule 10 does not face as much resistance in the stomach as does translational motion of capsule 10. Thus base electromagnet 34 does not have to be powerful, although the greater distance to capsule 10 (below feet to stomach) may require more magnetic force than the closer electromagnets 20, 22.

Base electromagnet 34 is placed below stationary disk 44 under person 50. Base electromagnet 34 is normally de-energized and turned off but can be turned on briefly to flip capsule 10. Base electromagnet 34 exerts a downward magnetic field in the vertical or Z direction.

Figure 14:
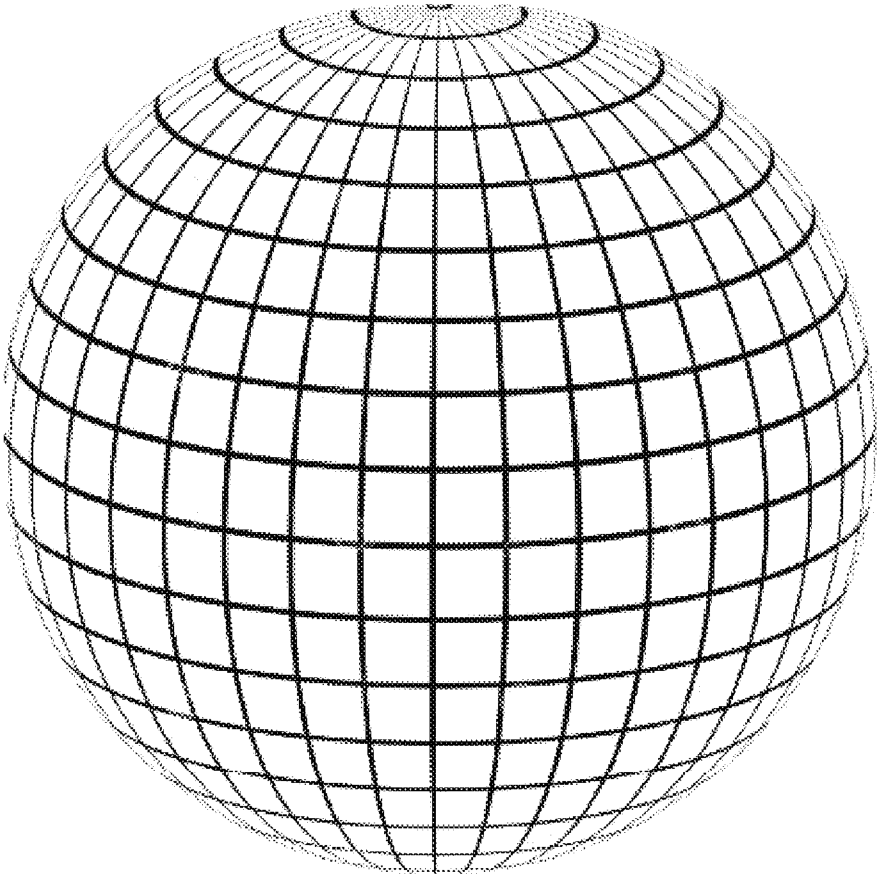
FIG. 14 is a polar coordinate map.

FIG. 14 is a polar coordinate map. VCSEL lasers 76, 86 can measure a distance that a laser beam travels from the laser source and back to the detector after reflecting off an object such as the stomach wall. By rotating ring 40 through 360 degrees and taking a series of laser range shots, the distance from capsule 10 to the stomach wall can be generated for a particular Z value or height. The Z values can be adjusted using actuators 30, 32 to different Z values to pitch capsule 10 up or down. Then the 360-degree laser range-finding can be repeated. Different pitches of capsule 10 can allow for mapping the entire polar coordinate space for each physical location of capsule 10.

Actuators 30, 32 can be activated to increase the Z value of capsule 10, and the 360 degree distance-measurement sequence repeated for each new location of capsule 10. Also, the current through electromagnets 20, 22 can be set to uneven values to allow for capsule movement in the X direction if desired. A polar coordinate map with measured distances to the stomach wall can be obtained for each of several physical locations of capsule 10 by rotating ring 40 through 360 degrees, and by pitching capsule 10 up and down by different angles. These polar maps can be merged to obtain an overall map of the stomach wall.

Also, both lasers 76, 86 can be used for each measurement, obtaining two range distances for two different points on the polar coordinate map. Since lasers 76, 86 are positioned at right angles to each other within capsule 10, The polar coordinate map may be obtained more quickly and more accurately than if only one laser is used.

Figure 15:
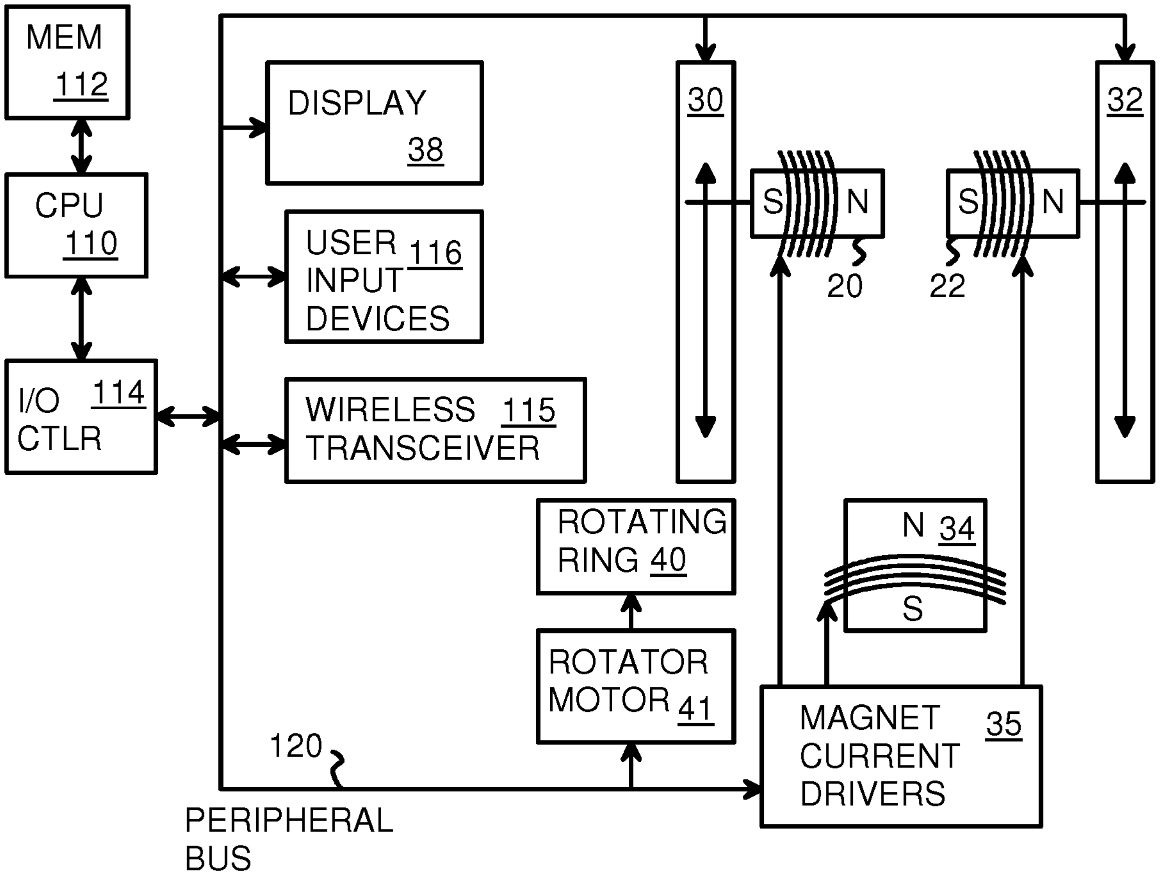
FIG. 15 is an electrical block diagram of the automated magnetic endoscopy machine.

FIG. 15 is an electrical block diagram of the automated magnetic endoscopy machine. An automated control program is loaded into memory 112 and executed by processor 110. This control program performs screening of a person by sequencing currents to electromagnets 20, 22, and adjusting Z positions of actuators 30, 32, and by rotating ring 40.

The control program sends one or more commands through I/O controller to peripheral bus 120 to magnet current drivers 35. These commands specify or adjust the current to electromagnet 20 or to electromagnet 22. These currents may be pulsed on for a specified period of time, or may remain on until another command turns the currents off. The direction of the current may be reversed to swap N and S poles of an electromagnet.

Sometimes capsule 10 is flipped to allow side camera 82 or side laser 86 to see a different hemisphere of the stomach. The control program sends a command through I/O controller to peripheral bus 120 to magnet current drivers 35 specifying the current to base electromagnet 34 when the control program desires to flip capsule 10.

At other times the control program sends a command through I/O controller to peripheral bus 120 to motor 41 that causes rotating ring 40 to rotate. The amount of rotation may be specified by the command, or may be determined by an amount of time that motor 41 is activated, with the control program keeping track of the rotational position of rotating ring 40.

When the Z position is to be adjusted, either to increase or decrease the height of capsule 10, or to pitch it up or down, the control program sends one or more commands through I/O controller to peripheral bus 120 to actuator 30 or to actuator 32. This command can activate actuator 20 to increase or decrease the Z distance of electromagnet 20 by a specified amount, as an example. Alternatively, the amount of time and the direction of movement of actuator 30 can be specified in the command, and the time of activation converted to an expected Z distance. The control program can keep track or prior Z movements and of the current Z position and make adjustments as desired.

The control program also sends commands through I/O controller to peripheral bus 120 to display 38 to display information to the person being screened, and can read user inputs from user input devices 116, such as a plug in keyboard for diagnostics for use by a technician, or a simple start button or stop button for the person to press for starting screening.

Processor 110, memory 112, wireless transceiver 115, and I/O controller 114 are small in size and may be located in an assembly or housing for display 38, or may be placed in a housing under floor 42, or in another location within box 310. Magnet current drivers 35 may be one or more chips or electronic devices that are located in floor 42 or may be partitioned among left electromagnet assembly 31 and right electromagnet assembly 33 and base electromagnet 34. Other physical placements and variations are possible.

Figure 16:
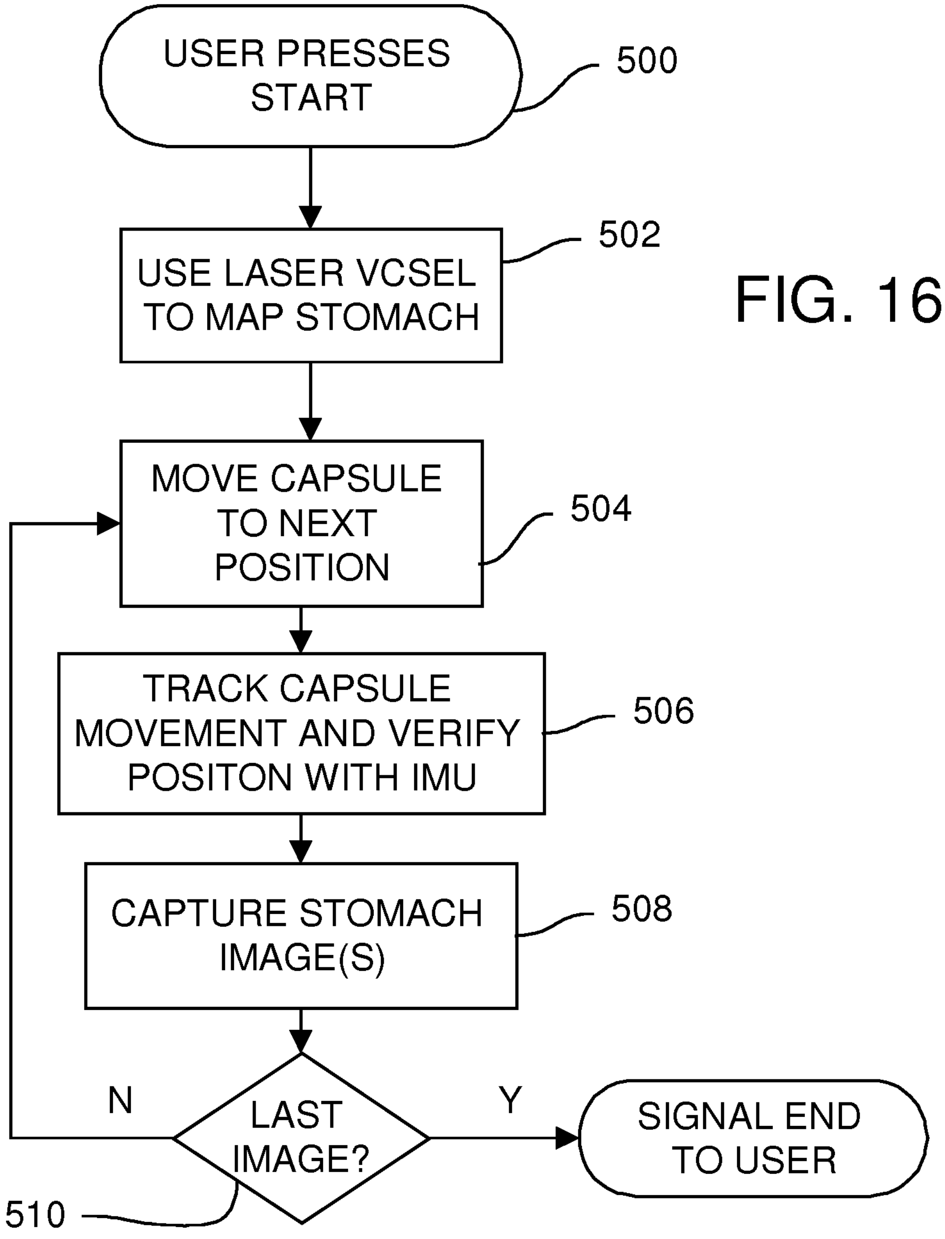
FIG. 16 is a flowchart of the automated magnetic endoscopy machine screening a person.

FIG. 16 is a flowchart of the automated magnetic endoscopy machine screening a person. The person has already swallowed capsule 10 just before the procedure begins, or is handed the capsule to swallow after stepping on stationary disk 44 and being clamped in. The user stands on stationary disk 44 and the person or an operator or other assistant adjusts the telescoping poles and side clamps to adjust for the person's height or physique. Then the person presses a start button to begin the screening routine, step 500.

The control program uses lasers 76, 86 to map the stomach walls, step 502. This may involve pitching capsule 10 up or down using electromagnets 20, 22, and rotating through the full circle for each pitch setting by using rotating ring 40 to map the full polar coordinate system. A polar map may be obtained for more than one physical location of capsule 10 by moving capsule 10 and repeating the rotational and pitch adjustments to obtain distances to the stomach wall from the laser.

Once the stomach wall map has been obtained, step 502, then the control program can move capsule 10 to different locations within the stomach. These locations can be selected based on the shape of the stomach. For example, certain parts of the stomach may be more prone to ulcers, and the control program can move capsule 10 close to these regions to obtain close-up images. Other selected locations may provide an unobstructed view of large portions of the stomach. Still other locations may be near the top or bottom of the stomach to permit capsule 10 to image these hard to examine regions. Also, if anomalies such as dark colored regions are found during imaging, the control program can move capsule 10 nearer to these regions for closer imaging when the battery life permits.

Figure 17:
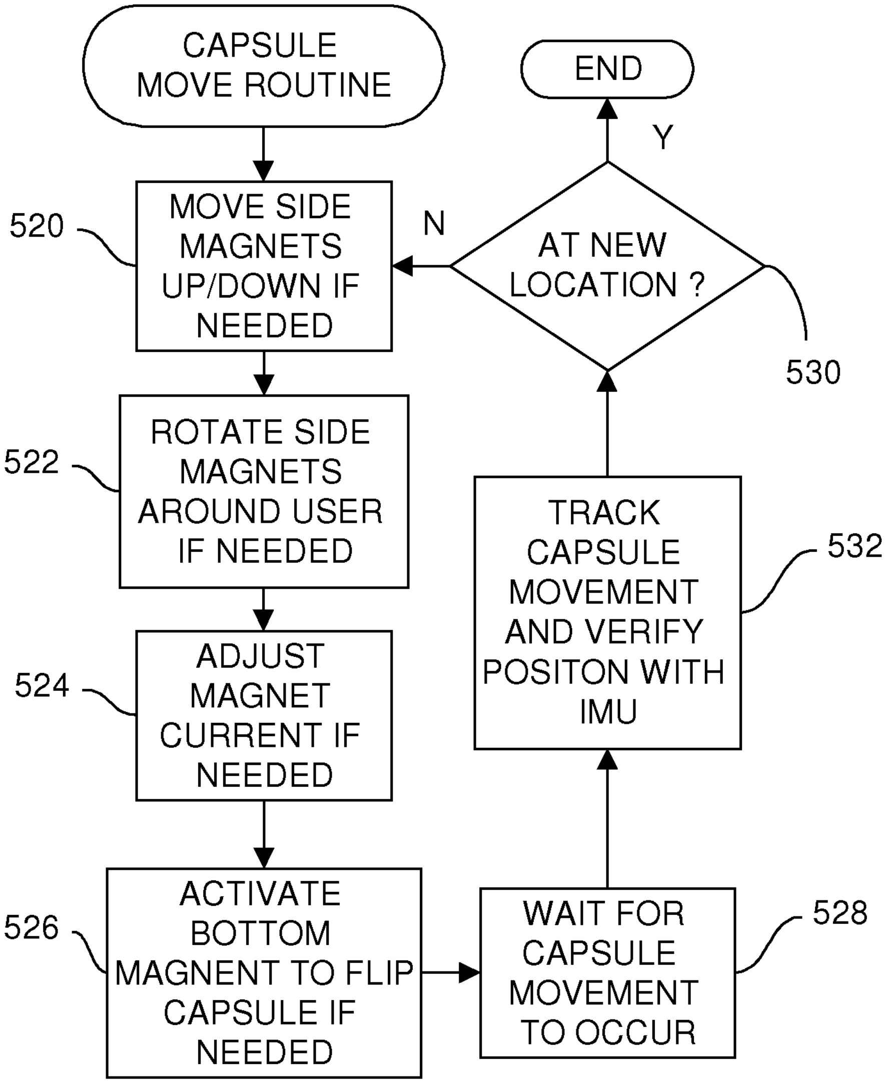
FIG. 17 is a flowchart of an autonomous capsule movement routine.

The capsule movement routine of FIG. 17 may be called for each desired movement of capsule 10, step 504. Movements may be divided into a sequence of smaller adjustments or steps, and various higher-level routines may call lower-level routines to perform control of magnet current drivers 35, actuators 30. 32, and motor 41.

Capsule 10 may be fitted with an Inertial Measurement Unit (IMU) that allows capsule 10 to report its estimated location by tracking forces, angular momentum, or orientation using various combinations of gyroscopes, accelerometers, magnetometers, or similar micro devices. The control program may also track the location of capsule 10, such as by tracking prior movements, or by verifying a current location by using lasers 76, 86 to verify distances to stomach walls. The control program in step 506 uses one or more of these methods to track the current location of capsule 10 within the map of the stomach obtained by laser distance-measurement in step 502.

Once capsule 10 is in a desired location, rotational angle, and pitch, an image is captured using front camera 72 with LEDs 74 turned on for illumination. Side camera 82 using LEDs 84 for illumination may also be used for imaging a different location that is 90-degrees from the image obtained by front camera 72. These captured images, step 508, are wirelessly transmitted from capsule 10 to the automated magnetic endoscopy machine and stored. The control program can analyze these images for abnormalities or image-capture errors, and can re-take faulty images or move capsule 10 closer to abnormalities for additional close-up image capture.

Movement of capsule 10 is repeated, step 504, location tracked, step 506, and new images captured, step 508, for a series of locations to image most of the stomach wall. Once all desired images have been captured, or the battery becomes too weak, step 510, the screening procedure ends and the control program sends a message to display 38 to tell the user that the screening procedure is done. The user can remove the side clamps and step off stationary disk 44. After a few hours the user will eliminate capsule 10, which can be discarded.

FIG. 17 is a flowchart of an autonomous capsule movement routine. This movement routine can be executed by a processor on the automated magnetic endoscopy machine and can be a sub-routine that is called by the control program during a screening procedure, such as by step 504 of FIG. 16.

The control program tracks the current position and determines the desired position to move capsule 10 to. The X, Y, Z desired movement vector can then be calculated by the control program. The X-Y movement can be converted to polar coordinates so that a rotational angle is calculated rather than a Y value for the movement vector.

When the desired movement vector includes a Z component, then the control program sends a command to actuators 30, 32 to adjust the Z distance, thus moving electromagnets 20, 22 up or down, step 520. When capsule 10 is to be pitched up or down, the Z values set for actuator 30 and for actuator 32 are different.

When the desired movement vector includes a rotational angle, then the control program sends one or more commands to activate motor 41 to rotate rotating ring 40 by the rotational angle in the desired movement vector, step 522.

When the desired movement vector includes an Xr component in the current rotational plane, then the control program sends a command to magnet current drivers 35 to adjust the ratio of currents to electromagnets 20, 22, step 524. This increases magnetic attraction in the Xr direction and allows capsule 10 to move in the Xr direction. Note that this Xr direction is for the current rotational plane, not the original X direction in the default plane when the rotational angle is non-zero.

When the control program desires to flip capsule 10 so that side camera 82 faces downward rather than upward, the control program sends a command to magnet current drivers 35 to pulse the current to base electromagnet 34, step 526. This current pulse causes base electromagnet 34 to pull downward on flip magnet 80 within capsule 10, causing capsule 10 to rotate along its longitudinal axis, and flip the upward facing camera to face downward, or vice-versa. Step 526 can be disabled if capsule 10 is pitched up or down rather than flat and parallel to base electromagnet 34.

After commands have been sent for any of the desired movement components in steps 520-526, then the control program waits for a period of time, step 528. The amount of time needed for movement to occur depends on several factors, such as the viscosity of stomach fluid, the distance of desired movement, the time required for physical movement of rotating ring 40 or of electromagnets 20, 22 in response to actuators 30, 32, etc. An estimate may be used for the time delay.

The control program checks the position of capsule 10 after sufficient time has elapsed for the desired movement, step 532. The position of capsule 10 can be verified using an IMU inside capsule 10 that transmits acceleration data wirelessly to the automated magnetic endoscopy machine in its control program. When capsule 10 is not at the desired position, step 530, then the control program may make further movements by adjusting the movement vector and repeating steps 520-532. When capsule 10 has reached the desired position, step 530, then the capsule movement subroutine ends and control returns to the main screening routine of FIG. 16.

Figure 18A:
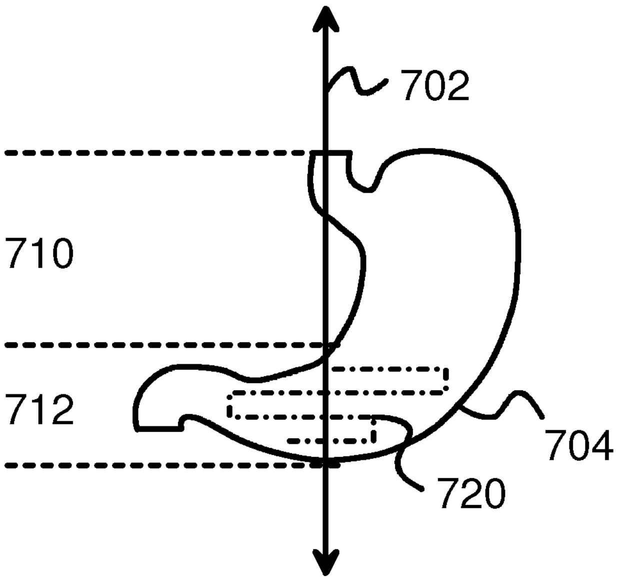
FIGS. 18A-18B show paths created by the control program that lie within the stomach map created from laser distance-measurement data.
Figure 18B:
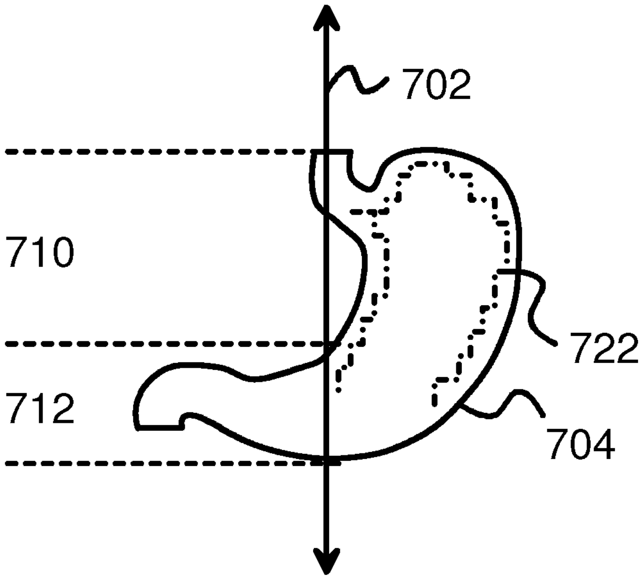

FIGS. 18A-18B show paths created by the control program that lie within the stomach map created from laser distance-measurement data. Once capsule 10 enters the stomach, the lasers measure distances to the stomach walls as the capsule moves within the stomach. The control program generates stomach map 704 which is a 3D map of the stomach calculated from the laser distance-measurement data and inertial dais from the capsule on it's location or movements. The control program can activate electromagnets 20, 22, actuators 30, 32, and motor 41 to adjust the position of capsule 10 within the stomach, or within an expected position of the stomach when the stomach map is incomplete, as laser distance-measurement data is being captured.

In FIG. 18A, the laser distance-measurement data and capsule inertial data has been used to generate stomach map 704. In lower region 712, rotational axis 702 is a vertical axis that rotating ring 40 rotates around, and this vertical axis typically passes through the person's head and abdomen, depending on the person's exact standing position and physique. While rotational axis 702 passes through the stomach, the non-symmetrical shape of the stomach causes rotational axis 702 to pass through only lower region 712 but not through upper region 710, other than a small portion by the esophagus. When control program creates path 720 that the capsule will follow through the stomach, the control program can rotate capsule 10 when it is near rotational axis 702. However, when capsule 10 is far from rotational axis 702, such as in upper region 710, rotation of rotating ring 40 could cause capsule 10 to hit the stomach wall.

The control program performs rotation primarily in lower region 712. The control program uses mostly X and Z motions when generating path 722 in upper region 710. In FIG. 18A, the control program generates path 720 by rotating the capsule when it is near rotational axis 702 in lower region 712, and also uses X and Z motions, being careful to only have movements that fall within the interion of stomach map 704. In FIG. 18B, the control program generates path 722 without fully rotating the capsule in upper region 710, and only uses partial rotations to adjust camera angle, and X and Z motions, being careful to only have movements that fall within the interior of stomach map 704. The control program may combine many paths 722 that each trace a different vertical slice of stomach map 702 in the 3D map. When rotation is needed, the control program can return capsule 10 to rotational axis 702 in lower region 712 for rotation, before returning to upper region 710. Many path and movement variations are possible.

ALTERNATE EMBODIMENTS

Several other embodiments are contemplated by the inventors. For example many combinations and variations of the control program, hardware, controllers, magnets, poles, clamps, and transportable box are possible. Box 310 may be fitted with handles and rollers for easier transport, and top 306 and side 304 may be hinged to swing open or may be removable. Box walls could be transparent to allow onlookers to watch the magnets rotate during the screening process and thus increase public interest in the procedure.

The automated magnetic endoscopy machine can be relatively small and portable. Box 310 can be a box or about 1.2 to 1.6 meters on each side. While side clamps have been described, the person may be restrained from moving by other restraint methods, such as straps, holsters, webbing, blocking, etc.

Telescoping poles to adjust for different heights of people may be manual or may be automated. Arrows or other indica may be provide to line up the pole height with the person's stomach, such as between a person's nipples and navel.

Since the control program selects what images to capture and maps the stomach to determine locations to move capsule 10 to, a skilled medical doctor is not needed to operate the automated magnetic endoscopy machine. Also, since the control program makes decisions about what areas to image, the screening procedure does not have to wait for a human doctor to examine the images and decide on the next movements for further imaging. The speed of the screening procedure can be much faster using the control program than when using a human doctor. This faster screening has the benefit of permitting a smaller battery to be used, with a reduction in the size of capsule 10, compared with human-controlled screening. A larger number of images may be automatically captured possibly providing for better screening.

When the remaining battery life is sufficient near the end of screening, the control program can take additional images of areas where an abnormality is detected in the earlier scan of images. The control program can use Artificial Intelligence (AI) or other tools and may offload images to a remote server for such processing. The remote server can respond with coordinates within the stomach map of areas of interest for the control program to take additional images before the battery dies.

The control program does not require human input. The control program maps the stomach wall and then adjusts the magnets to move capsule 10 through a sequence of locations within the confines of the stomach wall identified by the stomach wall map and captures images of the stomach wall from these various locations. The control program can screen these images for abnormalities, and take additional images when abnormalities are detected. Images with abnormalities can be flagged and sent to a medical doctor or technician for further evaluation, and the person can be referred to a doctor for a traditional endoscopy when such abnormalities are detected by the control program.

While two cameras 72, 82 and two lasers 76, 86 have been described for capsule 10, other embodiments may have only one camera or laser, or may have more than two. Capsule 10 may be simplified further or enhanced further. A hard plastic that is impervious to stomach acid may be used for the casing of capsule 10, with clear windows for cameras 72, 82 and LEDs 74, 84, and lasers 76, 86. Capsule 10 may be pill-shaped for easy swallowing.

While laser mapping and imaging of the stomach have been described, capsule 10 eventually passes through the intestines, and imaging of the intestines could also be performed when sufficient battery life is available. The more limited cross-sectional area of the intestines may hinder movement of capsule 10 compared with the larger stomach, and capsule 10 may rapidly move through the intestines regardless of external magnetic fields due to natural intestinal contractions and other processes. Thus the screening procedure may be more difficult to apply to colonoscopies, but is not impossible. Further research with the invention may permit extension to intestinal screening.

While rotating ring 40 through all 360 degrees has been described, this rotation may not require 360 separate measurements. For example, a laser distance measurement or camera image may be obtained only every 10 degrees, for a total of 36 measurements for the entire 360 degree rotation cycle. Fewer measurements may be used for higher latitude regions of the polar map than for equatorial regions that have a larger circumference. The field of view of the camera may affect the number of images per full rotation. A camera with a 45 degree field of view may capture an image for every 36 degrees of rotation, for a total of 10 imaged for a full circle, while a camera with a narrow 15 degree field of vision may require images every 10 degrees, for a total of 36 images for the full rotational circle. The amount of overlap between adjacent images can also be adjusted. Many optimizations are possible.

Various combinations of software, firmware, and hardware may be used to implement various functions and operations. Hardware may provide low-level control of actuators 30, 32, and software may use I/O writes to write commands and values into registers for actuators 30, 32 to control movement, or to magnet current drivers 35 to control current values. Hardware may decode commands and activate low-level control routines, such as to rotate or move components by a specified amount or for a specified time. Many variations and levels of control are possible.

Currents can be positive or negative currents, direct or alternating, and flow in either direction. Many second and third order magnetic and electrical effects may be present and may be significant, but adjusted for through benchmarking.

Poles do not have to by cylindrical, and telescoping or height adjustments may be performed by various mechanisms.

Terms such as up, down, above, under, horizontal, vertical, inside, outside, clockwise, counter-clockwise, etc. are relative and depend on the viewpoint and are not meant to limit the invention to a particular perspective. Devices may be rotated so that vertical is horizontal and horizontal is vertical, so these terms are viewer dependent.

The background of the invention section may contain background information about the problem or environment of the invention rather than describe prior art by others. Thus inclusion of material in the background section is not an admission of prior art by the Applicant.

Any methods or processes described herein are machine-implemented or computer-implemented and are intended to be performed by machine, computer, or other device and are not intended to be performed solely by humans without such machine assistance. Tangible results generated may include reports or other machine-generated displays on display devices such as computer monitors, projection devices, audio-generating devices, and related media devices, and may include hardcopy printouts that are also machine-generated. Computer control of other machines is another tangible result.

Any advantages and benefits described may not apply to all embodiments of the invention. When the word "means" is recited in a claim element, Applicant intends for the claim element to fall under 35 USC Sect. 112, paragraph 6. Often a label of one or more words precedes the word "means". The word or words preceding the word "means" is a label intended to ease referencing of claim elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC Sect. 112, paragraph 6. Signals are typically electronic signals, but may be optical signals such as can be carried over a fiber optic line.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. An automated magnetic endoscopy machine comprising:

a stationary disk that a person stands on for endoscopic screening;

a rotating ring that surrounds the stationary disk;

a motor for rotating the rotating ring around the stationary disk;

a first pole attached to the rotating ring, the first pole supporting a first electromagnet assembly having a first electromagnet that is movable in a Z direction by a first actuator, the Z direction being orthogonal to a plane of the rotating ring;

a second pole attached to the rotating ring, the second pole supporting a second electromagnet assembly having a second electromagnet that is movable in the Z direction by a second actuator;

a wireless receiver;

a capsule that is swallowed by the person and enters a stomach of the person, the capsule having a battery, a camera that captures images of the stomach, a wireless transmitter that transmits the images to the wireless receiver, and a primary magnet;

a processor executing a control program, the control program causing the capsule to move vertically in the Z direction by commanding the first actuator to move the first electromagnet up or down while sending a first current to energize the first electromagnet, and by commanding the second actuator to move the second electromagnet up or down while sending a second current to energize the second electromagnet, move horizontally in an X direction that is orthogonal to the Z axis by sending the first current to energize the first electromagnet and sending the second current to energize the second electromagnet, wherein the first current has a higher magnitude than the second current, causing the first electromagnet to exert a greater force on the capsule than a force exerted by the second electromagnet when horizontal movement is performed; and rotate around a Z axis, the Z axis passing through a center of the stationary disk and through a head and part of the stomach of the person, the control program sending a command to the motor to rotate the rotating ring by a radial angle while the first current is sent to the first electromagnet and the second current is sent to the second electromagnet;

wherein the control program sends a plurality of commands to the motor, actuators, and electromagnets to perform a plurality of movements of the capsule to trace a path through the stomach, wherein the control program receives images from the capsule as the capsule moves along the path through the stomach, whereby images of the stomach are automatically captured by the capsule as it is moved along the path by the control program controlling the motor, first electromagnet, second electromagnet, first actuator, and second actuator.

2. The automated magnetic endoscopy machine of claim 1 wherein the control program is further for pitching the capsule upward, out of a horizontal plane, by commanding the first actuator to move the first electromagnet to a Z distance from the stationary disk that is different than a Z distance from the stationary disk of the second electromagnet.

3. The automated magnetic endoscopy machine of claim 1 wherein the control program controls the motor, first electromagnet, second electromagnet, first actuator, and second actuator to cause the capsule to move along the path through the stomach without human input to select the path or the images captured by the capsule, wherein screening is automatic and does not require a medical doctor to control the automated magnetic endoscopy machine.

4. The automated magnetic endoscopy machine of claim 3 wherein the capsule further comprises:

a flip magnet having a magnetic axis that is orthogonal to a magnetic axis of the primary magnet; further comprising:

a base electromagnet under the stationary disk;

wherein the control program sends current to the base electromagnet, which generates a base magnetic field that acts upon the flip magnet to cause the capsule to flip orientation.

5. The automated magnetic endoscopy machine of claim 3 wherein the capsule further comprises a laser, the laser generating a laser beam that reflects off a wall of the stomach, the laser determining a distance from the capsule to the wall of the stomach from a reflected laser beam received by the laser;

wherein the control program sends commands to the motor, first electromagnet, second electromagnet, first actuator, and second actuator to move the capsule among multiple orientations to allow the laser to measure distances to multiple points on the stomach wall;

wherein the capsule sends the distances generated by the laser to the control program using the wireless transmitter;

wherein the control program uses the distances generated by the laser to construct a map of the stomach wall;

wherein the control program calculates the path through the stomach using the map of the stomach wall generated from distances determined by the laser, wherein the control program generates points along the path that are all enclosed by the stomach wall;

whereby the stomach wall is mapped by the laser and the map is used by the control program to generate the path within the stomach for image capture by the camera in the capsule.

6. The automated magnetic endoscopy machine of claim 5 wherein the laser comprises a Vertical-Cavity Surface-Emitting Laser (VCSEL).

7. The automated magnetic endoscopy machine of claim 5 wherein the control program activates the motor to rotate the rotating ring to cause the capsule to rotate along an arc around the Z axis, wherein the arc is limited by the control program to be within the stomach as defined by the laser mapping the stomach wall;

wherein the control program inhibits full rotation for upper regions of the stomach;

wherein the Z axis does not intersect the stomach for the upper regions of the stomach.

8. The automated magnetic endoscopy machine of claim 5 wherein the capsule further comprises:

an end camera, placed at an end of the capsule, for imaging along a longitudinal axis of the capsule;

a side camera, mounted to the printed circuit board, for imaging in a direction perpendicular to the longitudinal axis of the capsule;

a plurality of light emitting diodes to generate light that is reflected off the stomach wall for capture by the end camera or the side camera.

9. The automated magnetic endoscopy machine of claim 5 further comprising:

an enclosure that surrounds the automated magnetic endoscopy machine, the enclosure having an opening to allow the person to step into the enclosure and stand on the stationary disk;

wherein the enclosure fully encloses the automated magnetic endoscopy machine for transport, whereby the automated magnetic endoscopy machine is transportable.

10. The automated magnetic endoscopy machine of claim 9 further comprising:

armrests, situated at a distance above the stationary disk that is greater than a maximum height of the first and second electromagnet assembly, for receiving arms of the person to prevent injury from rotation of the first and second electromagnet assembly.

11. The automated magnetic endoscopy machine of claim 10 further comprising:

a display, situated higher than the armrests, for displaying information to the person during screening, the display receiving information from the control program for display to the person.

12. The automated magnetic endoscopy machine of claim 10 further comprising:

a first height adjustor for adjusting a height of the first pole before screening;

a second height adjustor for adjusting a height of the second pole before screening.

13. The automated magnetic endoscopy machine of claim 10 wherein the capsule further comprises an accelerometer for inertially tracking movements of the capsule, wherein inertial movements are transmitted over the wireless transmitter to the control program.

14. An automated endoscopy machine comprising:

a stationary platform that a person stands on for testing;

a rotating ring that rotates around person standing on the stationary platform, wherein an axis of rotation of the rotating ring passes through a head and a stomach of the person;

a first electromagnet mounted to a first actuator that adjusts a height of the first electromagnet, the first actuator mounted to the rotating ring by a first supporter;

a second electromagnet mounted to a second actuator that adjusts a height of the second electromagnet, the second actuator mounted to the rotating ring by a second supporter;

a capsule in the stomach of the person during testing, the capsule having a battery, wireless transceiver, a primary magnet along a longitudinal axis of the capsule, a camera, and a light source for the camera;

a wireless transceiver for receiving images of the stomach that are captured by the camera in the capsule;

a processor;

a first magnet current driver for generating a first current to the first electromagnet to cause the first electromagnet to generate a magnetic field that creates a movement force on the primary magnet inside the capsule;

a second magnet current driver for generating a second current to the second electromagnet to cause the second electromagnet to generate a magnetic field that creates a movement force on the primary magnet inside the capsule;

a control program executing on the processor, the control program moving the capsule along a movement line between the first electromagnet and the second electromagnet by commanding the first magnet current driver to increase the first current and by commanding the second magnet current driver to maintain or decrease the second current;

wherein the movement line is a line that passes through the first electromagnet and passes through the second electromagnet;

a rotation motor that rotates the rotating ring in response to a rotation command from the control program executing on the processor, wherein the movement line is rotated, allowing the capsule to rotate within the stomach;

wherein the control program moves the capsule vertically by commanding the first actuator to adjust the height of the first electromagnet, and by commanding the second actuator to adjust the height of the second electromagnet; and a plurality of movement commands issued by the control program that causes the capsule to move along a path within the stomach, wherein the control program commands the capsule to activate the camera to capture images at points along the path;

whereby the person is screened to capture stomach images automatically by execution of the control program, wherein the control program moves the capsule along the path and for automated image capture along the path.

15. The automated endoscopy machine of claim 14 further comprising:

a base electromagnet situated under the person;

wherein the capsule further comprises:

a flip magnet having a magnetic axis that is orthogonal to a magnetic axis of the primary magnet;

wherein the control program sends a current to the base electromagnet, which generates a base magnetic field that acts upon the flip magnet to cause the capsule to flip orientation, changing a field of view of the camera to a different location within the stomach.

16. The automated endoscopy machine of claim 14 wherein the control program pitches the capsule by commanding the first actuator to adjust the height of the first electromagnet to a different height than the height of the second electromagnet set by the second actuator;

wherein pitching the capsule changes a field of view of the camera within the stomach.

17. The automated endoscopy machine of claim 14 wherein the first electromagnet and the second electromagnet are located about 180 degrees apart on the rotating ring;

wherein the first supporter and the second supporter are mounted to opposite sides of the rotating ring.

18. The automated endoscopy machine of claim 14 wherein the capsule further comprises:

an inertial monitoring unit that has at least one accelerometer to detect movement of the capsule, the inertial monitoring unit sending movement information to the control program over the wireless transceiver;

a laser for bouncing a laser beam off an inner sidewall of the stomach, the laser having a range detector that determines a distance from the capsule to a wall of the stomach;

wherein the capsule transmits distances obtained from the laser range detector to the control program using the wireless transceiver;

a stomach map generated by the control program from the distances and the movement information transmitted from the capsule;

wherein the control program generates the path to have only points that are within an interior of the stomach as indicated by the stomach map.

19. A standing endoscopy screening machine comprising:

a stationary place that a person stands on for endoscopy screening;

a rotating ring that rotates around a Z axis that passes thought a head and a portion of a stomach of the person standing on the stationary place;

a motor for rotating the rotating ring around the Z axis;

a first supporter attached to the rotating ring, the first supporter supporting a first electromagnet assembly having a first electromagnet that is movable in a Z direction by a first actuator, the Z direction being orthogonal to a plane of the rotating ring;

a second supporter attached to the rotating ring, the second supporter supporting a second electromagnet assembly having a second electromagnet that is movable in the Z direction by a second actuator;

a wireless transceiver;

a capsule that is swallowed by the person and enters a stomach of the person, the capsule having a battery, a camera that captures images of the stomach, a wireless transmitter that transmits the images to the wireless transceiver, and a primary magnet;

a processor executing a control program, the control program causing the capsule to move vertically in the Z direction by commanding the first actuator to move the first electromagnet up or down while sending a first current to energize the first electromagnet, and by commanding the second actuator to move the second electromagnet up or down while sending a second current to energize the second electromagnet, move horizontally in an X direction that is orthogonal to the Z axis by sending the first current to energize the first electromagnet and sending the second current to energize the second electromagnet, wherein the first current has a higher magnitude over time than and the second current, causing the first electromagnet to exert a greater force on the capsule than a force exerted by the second electromagnet when horizontal movement is performed; and rotate around the Z axis, the control program sending a command to the motor to rotate the rotating ring by a radial angle;

wherein the control program sends a commands to the motor, actuators, and electromagnets to perform movements of the capsule to trace a path through the stomach, wherein the control program receives images from the capsule as the capsule moves along the path through the stomach, whereby images of the stomach are automatically captured by the capsule as it is moved along the path by the control program controlling the motor, first electromagnet, second electromagnet, first actuator, and second actuator.

20. The standing endoscopy screening machine of claim 19 wherein the capsule further comprises:

an inertial monitoring unit that has at least one accelerometer to detect movement of the capsule, the inertial monitoring unit sending movement information to the control program over the wireless transceiver;

a laser for bouncing a laser beam off an inner sidewall of the stomach, the laser having a range detector that determines a distance from the capsule to a wall of the stomach;

wherein the capsule transmits distances obtained from the laser range detector to the control program using the wireless transceiver;

a stomach map generated by the control program from the distances and the movement information transmitted from the capsule;

wherein the control program generates the path to have only points that are within an interior of the stomach as indicated by the stomach map;

wherein the control program commands the motor to rotate the rotating ring when the capsule is in a lower portion of the stomach that the Z axis intersects, the control program inhibiting full rotation for upper regions of the stomach that the Z axis does not intersect.

* * * * *